(12) United States Patent
Dahia

(10) Patent No.: US 11,690,834 B2
(45) Date of Patent: Jul. 4, 2023

(54) COMPOSITION, USES, AND METHODS OF TREATING SPINAL DISC DEGENERATION THROUGH SONIC HEDGEHOG SIGNALING PATHWAY

(71) Applicant: New York Society For the Relief Of The Ruptured and Crippled, Maintaining the Hospital for Special Surgery, New York, NY (US)

(72) Inventor: Chitra Dahia, New York, NY (US)

(73) Assignee: New York Society for the Relief of the Ruptured and Crippled, maintaining the Hospital for Special Surgery, New York, NY (US)

( * ) Notice: Subject to any disclaimer, the term of this patent is extended or adjusted under 35 U.S.C. 154(b) by 146 days.

(21) Appl. No.: 16/625,164

(22) PCT Filed: Jun. 23, 2018

(86) PCT No.: PCT/US2018/039178
§ 371 (c)(1),
(2) Date: Dec. 20, 2019

(87) PCT Pub. No.: WO2018/237368
PCT Pub. Date: Dec. 27, 2018

(65) Prior Publication Data
US 2021/0128540 A1    May 6, 2021

Related U.S. Application Data

(60) Provisional application No. 62/524,121, filed on Jun. 23, 2017, provisional application No. 62/631,184, filed on Feb. 15, 2018.

(51) Int. Cl.
*A61K 31/4436* (2006.01)
*A61P 21/00* (2006.01)
*A61K 45/06* (2006.01)

(52) U.S. Cl.
CPC .......... *A61K 31/4436* (2013.01); *A61K 45/06* (2013.01); *A61P 21/00* (2018.01)

(58) Field of Classification Search
CPC .......................... C07D 405/12; A61K 31/4436
See application file for complete search history.

(56) References Cited

U.S. PATENT DOCUMENTS

| 9,061,997 | B2* | 6/2015 | Ruat ....................... A61P 15/08 |
| 2004/0230309 | A1 | 11/2004 | DiMauro et al. |
| 2006/0078499 | A1* | 4/2006 | Hen .................... A61K 49/0008 424/9.2 |
| 2008/0138379 | A1 | 6/2008 | Jennings-Spring |
| 2010/0034781 | A1* | 2/2010 | Parhami .................. A61P 17/14 424/93.7 |
| 2011/0172233 | A1 | 7/2011 | Peng et al. |
| 2014/0275025 | A1 | 9/2014 | Anderskewitz et al. |
| 2016/0143984 | A1 | 5/2016 | Chen et al. |
| 2017/0065745 | A1 | 3/2017 | Brown et al. |

FOREIGN PATENT DOCUMENTS

| JP | 2017511153 A | 4/2020 |
| WO | 2015143342 A1 | 9/2015 |

OTHER PUBLICATIONS

Dahia et al. PLoS One, 2012, 7(4), e35944.*
Winkler et al. PLoS One, 2014, 9(6), e98444/1-e98444/12.*
Dahia et al.: "Shh Signaling from the Nucleus Pulposus Is Required for the Postnatal Growth and Differentiation of the Mouse intervertebral Disc", PLOS One, vol. 7, No. 4, Apr. 2012 (Apr. 1, 2012), pp. 1-15, XP055555501.
Risbud et al.: "Notochordal Cells in the Adult Intervertebral Disc: New Perspective on an Old Question", Crit Rev Eukaryot Gene Expr., vol. 21, No. 1, 2011, pp. 29-41.
Winkler et al.: "Wnt Signaling Activates Shh Signaling in Early Postnatal intervertebral Discs, and Re-Activates Shh Signaling in Old Discs in the Mouse", PLoS One 9(6): e98444 (Jun. 2014).
Dahia, C. et al: "In Vitro Model System to Study Mouse Intervertebral Disc Growth," The Spine Journal, Elsevier, Amsterdam, NL, vol. 10, No. 9, Sep. 1, 2010, p. S138, XP027272495, ISSN: 1529-9430 [retrieved on Sep. 1, 2010] *the whole document*.
Hadden, Kyle M.: "Hedgehog Pathway Agonism: Therapeutic Potential and Small-Molecule Development," Chemmedchem, vol. 9, No. 1 (Nov. 7, 2013), pp. 27-37, XP055628960, DE ISSN: 1860-7179, DOI: 1002/cmdc. 201300358 *the whole document*.
Belteki, G, et al., "Conditional and inducible Transgene Expression in Mice Through the Combinatorial Use of Cre-Mediated Recombination and Tetracycline Induction", Nucleic Acids Research, 2005, 33,e51.
Choi, K.S., "Identification of Nucleus Pulposus Precursor Cells and Notochordal Remnants in the Mouse: Implications for Disk Degeneration and and Chordoma Formation", 2008, Dev. Dyn 237, pp. 3953-3958.
Collaborators, G. B. D. D. H., "Global, Regional, and National Disability-Adjusted Life Years (DALYs) for 306 Diseases and Injuries and Healthy Life Expectancy (HALE) for 188 Countries, 1990-2013: Quantifying the Epidemiological Transkation", Lancet, 2015, 386, pp. 2145-2191.
Dahia, Chitra, Conditional Genetic Mouse Models Targeting Shh Signaling to Study Intervertebral Disc Aging and Disease, ORS 2017 Annual Meeting Poster No. 1815.
Dahia, C. L., Mahoney, E. J., Durrani, A. A. and Wylie, C. Intercellular signaling pathways active during intervertebral disc growth, differentiation, and aging. Spine, 34, 456-462, 2009.
Dahia, CL, Mahoney EJ, Durrani AA, Wylie C. Postnatal growth, differentiation, and aging of the mouse intervertebral disc. Spine, vol. 34, No. 5, 447-55, 2009.
Harie, B. D. et al., "Evidence for an Expansion-Based Temporal Shh Gradient in Specifying Vertebrate Digit Identities", Cell, 2004, 118, 517-528.

(Continued)

*Primary Examiner* — Rei Tsang Shiao
(74) *Attorney, Agent, or Firm* — Ballard Spahr LLP

(57) ABSTRACT

Presented herein are methods for treating spinal disc degeneration (SDD) by administering to a subject in need thereof, an amount of a SHH signaling pathway activator effective for treating the subject.

14 Claims, 18 Drawing Sheets

(56) References Cited

OTHER PUBLICATIONS

Figure 1:
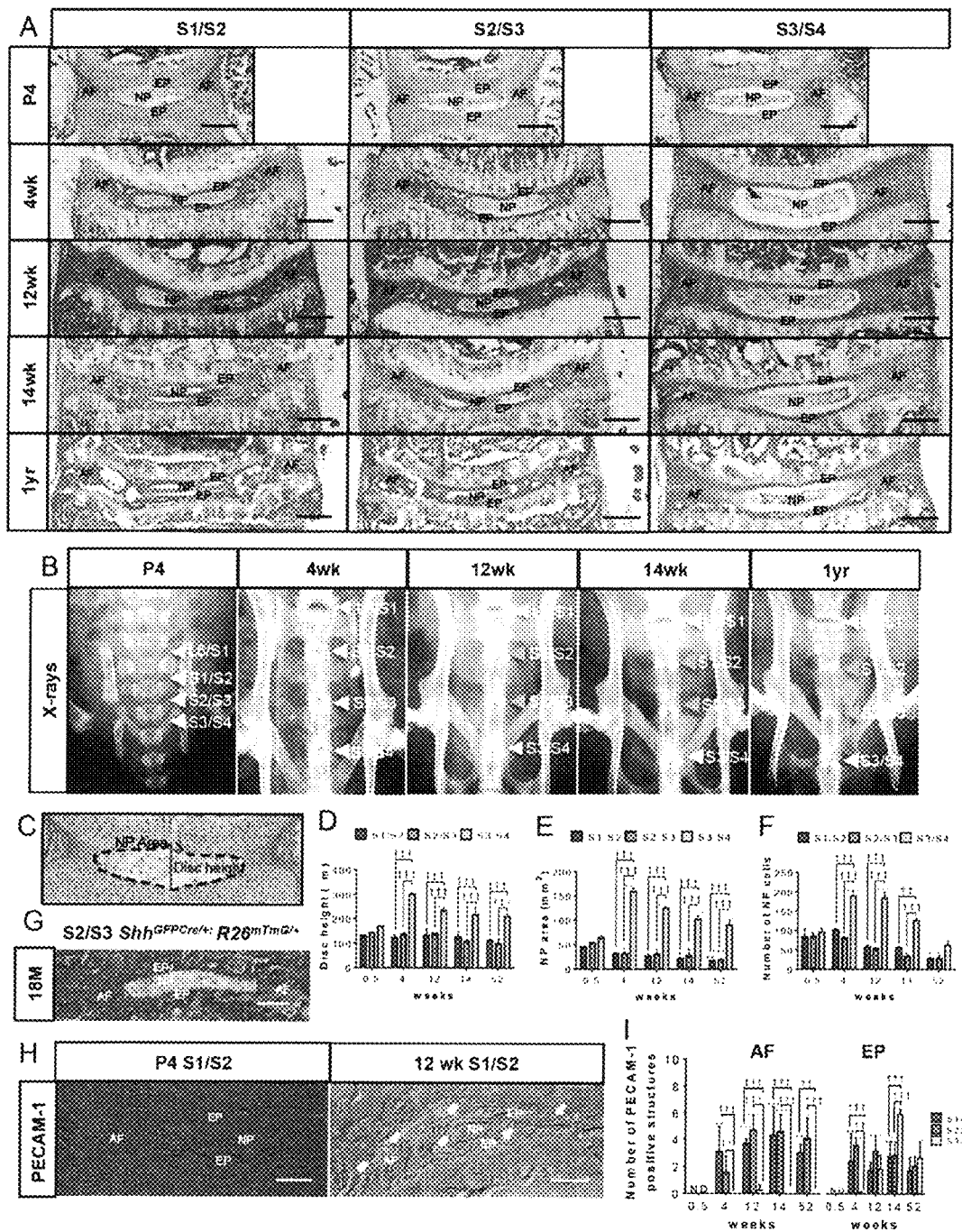

Hartvigsen, J. et al., "What Low Back Pain Is and Why We Need to Pay Attention", Lancet, 2018.
Hoy, D. et al. "A Systematic Review of the Global Prevalance of Low Back Pain", Arthritis and Rheumatism, 2012, 64, 2028-2037.
Kauppila, L. I. (1995). Ingrowth of blood vessels in disc degeneration. Angiographic and histological studies of cadaveric spines. J Bone Joint Surg Am 77, 26-31.
Lewis, P.M. et al., "Cholesterol Modification of Snic Hedgehog is Required for Long-Range Signaling Activity and Effective Modulation of Signaling by Ptc1", 2001, Cell, 105, 599-612.
McCann, M.R. et al., "Tracing Notochord-Derived Cells Using a Noto-Cre Mouse: Implications for Intervertebral Disc Devlopment", Disease Models & Mechanisms, 2012, 5, 73-82.
Means, A.L. et al., "A CK19(CreERT) Knockin Mouse Line Allows for Conditional DNA Recombination in Epithelial Cells in Multiple Endodermal Organs", Genesisi, 2008, 46, 318-323.
Miller, L. A. et al., "Role of Sonic Hedgehog in Patterning of Tracheal-Bronchial Cartilage and the Peripheral Lung", Dev Dyn, 2004, 231, 57-71.
Muzumdar, M.D. et al, "A Global Double-Fluorescent Cre Reported Mouse", Genesis, 2007, 45, 593-605.
Urban J. P. et al., "Degeneration of the Intervertebral Disc", Arthritis Res Ther, 2003, 5, 120-130.
Vergroesen, P. P. et al., "Mechanics and Biology in Intervertebral Disc Degeneration: A Vicious Circle", Osteoarthritis and Cartilage, 2015, 23, 1057-1070.

* cited by examiner

COMPOSITION, USES, AND METHODS OF TREATING SPINAL DISC DEGENERATION THROUGH SONIC HEDGEHOG SIGNALING PATHWAY

FUNDING STATEMENT

This invention was made with government support under 1R01AR065530-01A1 awarded by the National Institute of Health. The government has certain rights in the invention.

FIELD OF THE INVENTION

The present disclosure is directed to compositions, uses, and methods for the treatment of spinal disc degeneration with activators of sonic hedgehog signaling in a subject in need thereof.

BACKGROUND

Degenerative Disc Disease and Treatments

Degenerative disc disease and associated lower back pain is one of the top causes of pain and affects some 70% to 85% of the population in developed countries. Current treatments for degenerative disc disease focus on minimizing pain, stabilizing the spine, and improving or maintaining mobility. Treatments typically include some combination of pain and inflammation management techniques such as steroid injections and pain relievers, physical therapy, losing weight, and surgery. None of these treatments cure or prevent the degenerative disease.

Therefore, disc degeneration represents an important and unmet clinical need requiring more effective management. Currently prescribed therapies are only moderately effective, palliative, and/or invasive. The development of a pharmaceutical, relatively noninvasive composition which can treat disc degeneration would be beneficial.

Disc Anatomy and Physiology

The spinal disc is composed of three main cellular structures: the central nucleus pulposus (NP), the outer annulus fibrosus (AF), and the adjacent endplate (EP). The NP is derived from a homogenous population of SHH-derived embryonic notochordal cells (Choi 2008), and the AF and EP originate from the syndectome and sclerotome respectively. Degeneration of the disc is associated with hypocellularity of the disc, loss of disc height, and loss of extracellular matrix (ECM) proteins (Urban and Roberts, 2003; Vergroesen et al., 2015) like aggrecan and glycosaminoglycans.

Studies show that NP cells from young and healthy mouse continue to express notochordal markers like sonic hedgehog (SHH) and Brachyury (Bra) (Dahia 2009a, Dahia 2009b, Dahia 2012, Winkler 2014) and CK19 (Dahia 2012 and Winkler 2014). SHH belongs to the Hedgehog family of proteins which also include Indian hedgehog (IHH) and Desert Hedgehog (DHH). All hedgehog proteins act by the same receptors: patched1 (PTCH1) and smoothened receptor (SMO), and operate through the same signal transduction pathway involving GLI transcription factors. PTCH1 and Gli1 are known downstream targets of hedgehog signaling, and changes in their expression levels give insight to the status of hedgehog pathway. Structural changes in the SMO either following binding of a hedgehog protein to PTCH1 receptor; or using small molecule agonist of hedgehog pathways like Smoothened Agonist (SAG), or purmorphamine, or using its conditional allele known as SmoM2 in the mouse can activate the hedgehog signaling downstream of the ligand.

SHH is the only Hedgehog family member expressed in the intervertebral disc (Dahia et al., 2012). SHH is critical for proliferation and maintenance of the NP cells and their molecular markers like the T-box transcription factor Brachyury (Bra) and CK19, surrounding annulus fibrosus (AF) and end plates (EP) of the disc, and differentiation of the entire disc by way of production of extracellular matrix (ECM) markers in young mouse intervertebral discs. However, the expression of these markers decreases with age in mice (Dahia et al., 2009a; Dahia et al., 2009b; Winkler et al., 2014). SHH positively regulates TGF-beta pathway, but antagonizes BMP and canonical Wnt signaling pathway (Dahia 2012).

In mice, the expression of SHH and the response thereto dramatically decreased from postnatal day four (P4) to one year of age, and is associated with reduced expression of NP markers like Bra, and ECM proteins. When a one-year-old mouse disc is reactivated using BIO, small molecule agonist of canonical Wnt signaling in vitro, the stimulation of Hedgehog signaling and ECM production are increased (Winkler 2014). Not observed upon activation of the canonical Wnt signaling pathway was an increase in cell proliferation in a one-year-old mouse disc. (Winkler 2014)

SUMMARY

Disclosed herein are methods of preventing, reversing, ameliorating and/or treating spinal disc degeneration (SDD) or symptoms thereof in subjects in need thereof through the sonic hedgehog signaling pathway within nucleus pulposus cells of the disc.

In one aspect, provided herein are methods of treating a SDD in a subject, comprising administering to a subject in need thereof a composition comprising an amount of a sonic hedgehog signaling pathway activator to treat, reverse, and/or ameliorate the symptoms of, particularly the pain and/or impaired mobility associated with, or prevent SDD. In certain embodiments, the sonic hedgehog signaling pathway activator is a smoothened agonist.

In various embodiments, the administration comprises: administering about 2 to 30 mg/kg, specifically about 5 mg/kg to 10 mg/kg, 10 mg/kg to 15 mg/kg, 15 mg/kg to 20 mg/kg, 20 mg/kg to 25 mg/kg, or 20 mg/kg to 30 mg/kg once daily, twice daily, or even three times daily. The SHH signaling pathway activator may be formulated in an oral dosage form or an injectable form. In an injectable form for localized administration, the dosage may be reduced in account of the localized delivery. In certain embodiments, particularly for use by localized, disc injection, SHH activator is administered at a dose concentration of about 0.5 mg/ml to about 3 mg/ml.

In one aspect of the invention methods are provided for in situ regeneration of disc tissue, including stimulating the proliferation of NP cells, by administering an SHH signaling activator to an individual in need of treatment in an amount effective to regenerate said disc tissue.

In another aspect, provided herein are methods of treating intervertebral disc degeneration at one or more intervertebral discs in a subject, the method comprising administering an amount of a sonic (SHH) signaling pathway activator effective for treating intervertebral disc degeneration.

In another aspect, provided herein are compositions for use in the treatment of intervertebral disc degeneration comprising an effective amount of a sonic hedgehog (SHH) signaling pathway activator.

In another aspect, provided herein are uses of a sonic hedgehog (SHH) signaling pathway activator for the manufacture of a medicament for the treatment of intervertebral disc degeneration.

In yet another aspect, provided herein are methods for repairing or improving the function of an intervertebral disc in a subject, the method comprising administering an amount of a sonic (SHH) signaling pathway activator effective for repairing or improving the function of an intervertebral disc in the subject.

In another aspect, provided herein are compositions for use in repairing or improving the function of an intervertebral disc in a subject, the composition comprising an amount of a sonic (SHH) signaling pathway activator effective for repairing or improving the function of an intervertebral disc in the subject.

In another aspect, provided herein are uses of a sonic (SHH) signaling pathway activator for the manufacture of a medicament for repairing or improving the function of an intervertebral disc in a subject.

In yet another aspect, provided herein are methods for alleviating one or more symptoms of an intervertebral disc degeneration in a subject, the method comprising administering an amount of a sonic (SHH) signaling pathway activator effective for alleviating one or more symptoms of an intervertebral disc degeneration in the subject.

In another aspect, provided herein are compositions for use in alleviating one or more symptoms of an intervertebral disc degeneration in a subject, the composition comprising an amount of a sonic (SHH) signaling pathway activator effective for alleviating one or more symptoms of an intervertebral disc degeneration in the subject.

In another aspect, provided herein are uses of a sonic (SHH) signaling pathway activator for the manufacture of a medicament for alleviating one or more symptoms of an intervertebral disc degeneration in a subject. Other embodiments are disclosed infra.

FIGURES

FIG. 1. Formation of mouse sacrum. (A) is arranged in a tabular form with H and E stained mid-coronal section of the three levels of sacral discs (columns) from mice of different ages (rows). (B) Shows X-ray images of sacral spine at ages corresponding to (A). (C) Schema for morphometric analysis. (D-F) graphs representing quantification of the morphometric parameters; (D) measurement for disc height; (E) NP area; and (F) number of NP cells quantified in this study. (G) S2/S3 disc from 18 month old SHH$^{GFPCTe/+}$, -R26$^{mTmG}$ line. (H) S1/S2 discs from P4 and 12 weeks stained for PECAM-1. (I) Number of PECAM-1+ vascular structure in AF and EP with aging. H=height. Mean±s.d., N=3 each, for each time point. Significance was calculated using one-way ANOVA test. Scale bars=200 μmin A, 100 μmin G and H. Images in Bare presented not to scale. Nuclei are counter-stained with DAPI in G and Hand images are captured using DIC filter.

Figure 2:
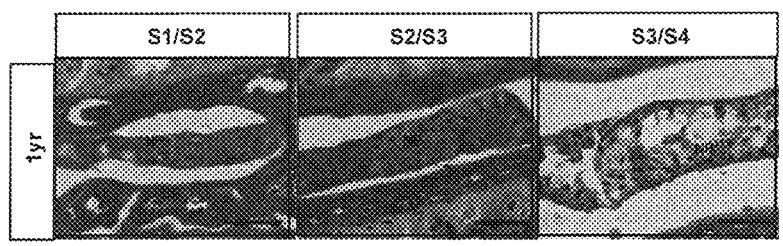

FIG. 2. Cell proliferation and cell death in mouse sacrum. (A) Representative image of Ki67 staining (white arrows) on P4 S1/S2 disc. (B) Quantification of percentage of Ki67+ve cells in NP and AF for all sacral levels at different ages. (C) Representative image of TUNEL staining (white arrows) on 12 weeks S1/S2 discs. (D) Quantification of percentage of TUNEL+ve cells in NP and AF for all sacral levels at different ages. Mean±s.d. N=3 each. One-way ANOVA test. Scale bars=100 μm.

Figure 3:
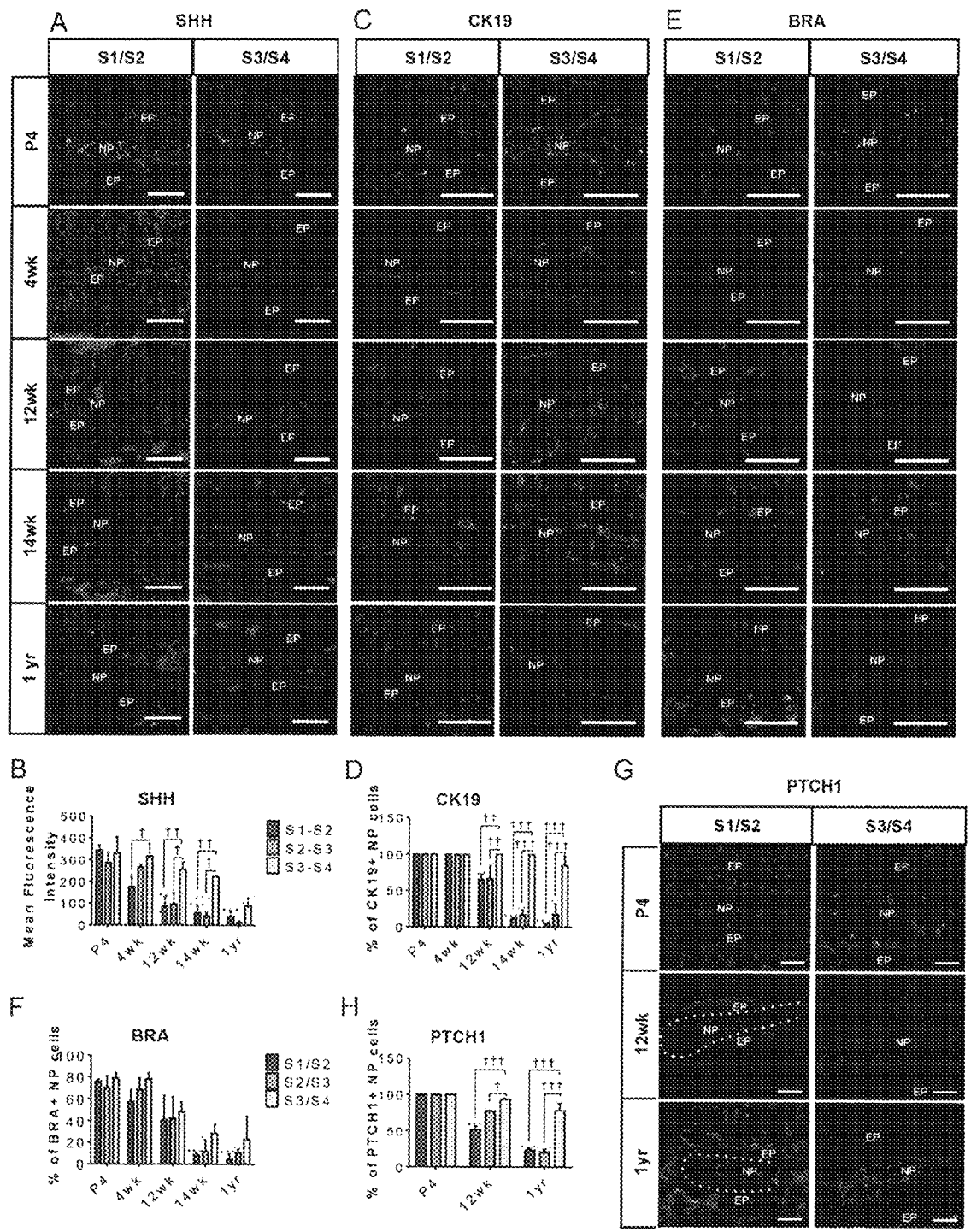

FIG. 3. Expression of SHH targets and notochordal markers in mouse sacral NP cells with aging. Immunofluorescence for notochordal/NP markers: SHH (A); CK19 (B); and Bra (C) in the S1/S2, and S3/S4 discs with age. N=3 each. Scale bars=100 μm. Nuclei are counterstained with DAPI in all images.

Figure 4:
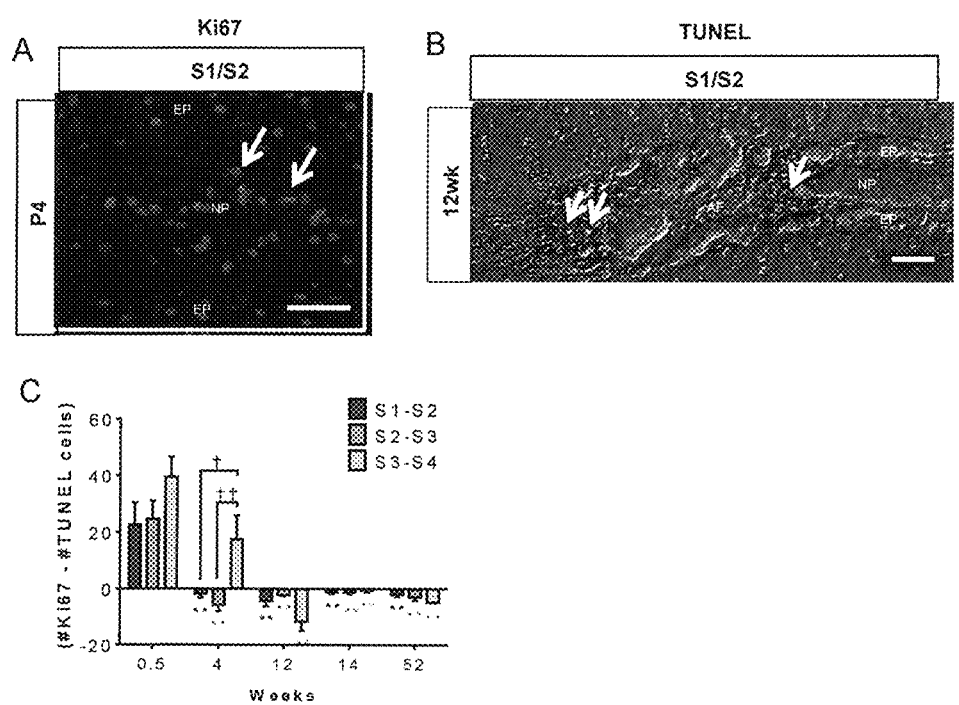

FIG. 4. Quantification of immunofluorescence staining for SHH targets and NP markers. (A) Quantification of mean immunofluorescence intensities for SHH (A) and CK19 (B) in S1/S2, S2/S3, and S3/S4 discs with age. (C) shows quantification of percentage of Bra+ve cells in the NP of S1/S2, S2/S3, and S3/S4 discs with age. Mean±s.d., N=3 each. One-way ANOVA test.

Figure 5:
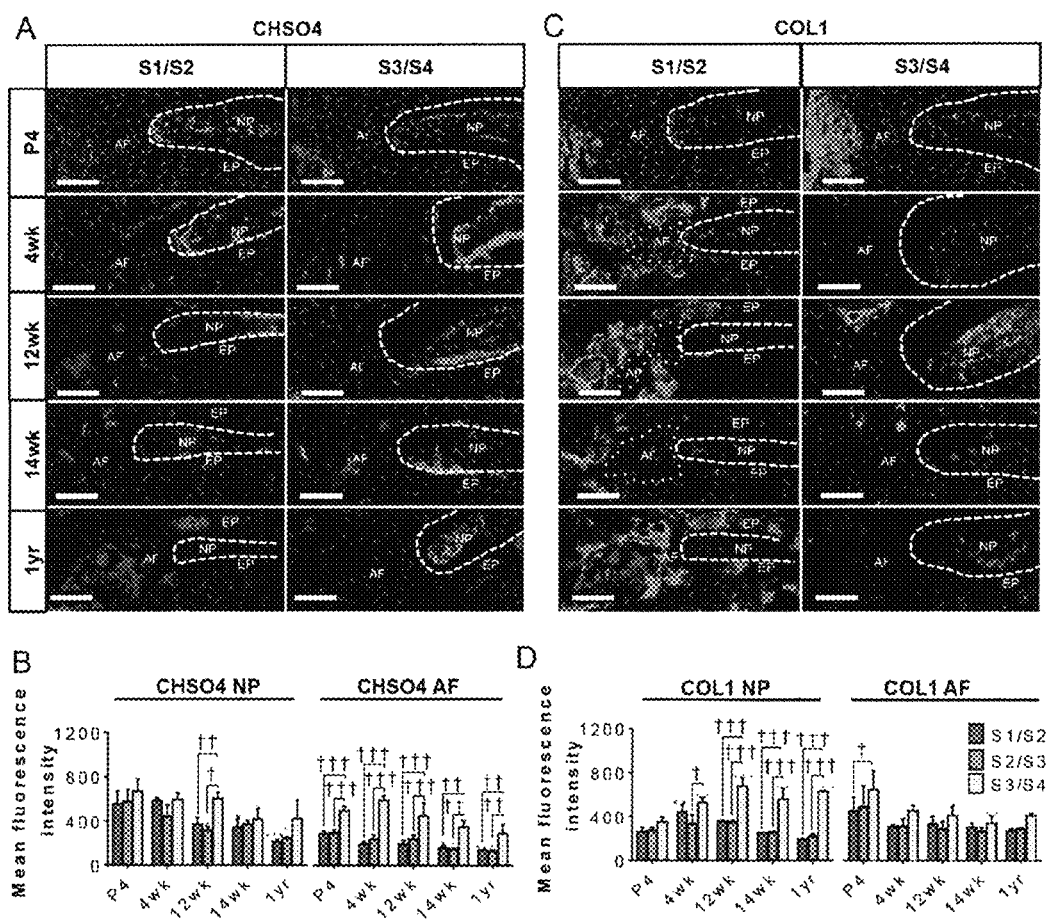

FIG. 5. Expression of SHH targets and ECM markers in sacral IVD with aging. This figure is in a tabular form. (A and B) shows the immunostaining for CHSO4 (A), and COL1 (B) in the S1/S2 and S3/S4 discs at different ages. N=3 each. Scale bar=100 μm. Nuclei are counterstained with DAPI in all images.

Figure 6:
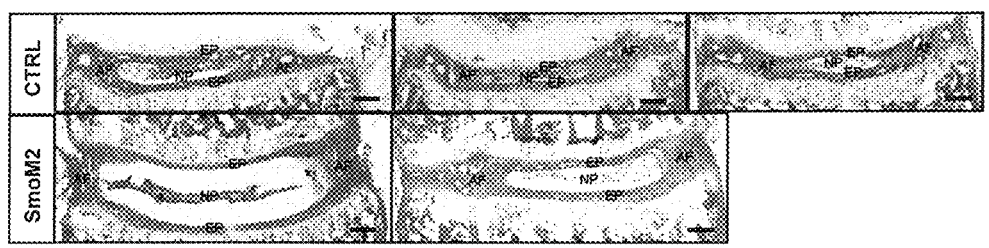

FIG. 6. Quantification of immunofluorescence intensities for SHH targets and ECM markers. (A) Quantification of mean immunofluorescence intensities for CHSO4 (A) and COL1 (B) in S1/S2, S2/S3, and S3/S4 discs with age. Mean±s.d., N=3 each. One-way ANOVA test.

Figure 7:
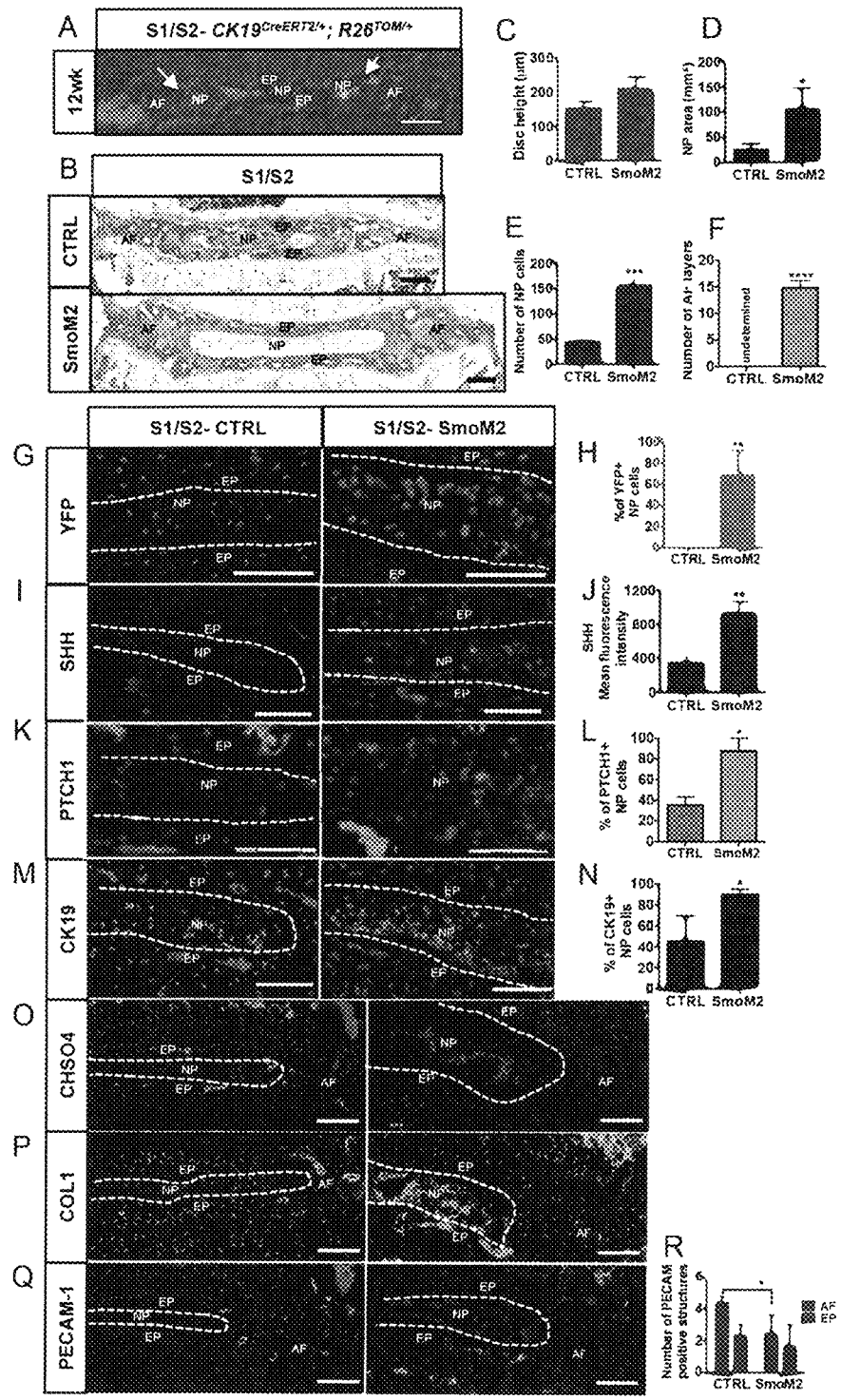

FIG. 7. Constitutive activation of SmoM2 in the NP cells re-activates the sacral disc. (A) Shows the coronal section of S2/S3 discs from CK19$^{CreER/J+}$; R26$^{mTmG}$ gavaged at four months of age and analyzed 48 hours later. (B) shows the schema for activation of SHH signaling in NP cells. The data is presented from the analysis of S1/S2 discs. (C) H and E staining of mid-coronal section from control (CTRL) and SmoM2 littermate. (D-G) shows quantification of morphometric parameters disc height (D); area occupied by the NP cells (E); number of NP cells (F); and number of layers in AF (G) in the sacral discs of the SmoM2 group compared to littermate controls. (H and I) Immunostaining and quantification of YFP+NP cells in SmoM2 and control discs. (J-O) shows data from immunostaining for SHH, and its downstream targets and their quantification: (J and K) SHH; (Land M) CK19; (N) CHSO4; and (O) COL1 expression in S1/S2 discs from controls and SmoM2 mice. (P and Q) shows immunostaining and quantification of PECAM-1 positive structures in the AF and EP of SmoM2 and control mouse discs. Mean±s.d. N=4 Controls, N=3 SmoM2. Unpaired two-tailed t-test. Scale bars=100 Nuclei are counter-stained with DAPI in the immunostaining images.

Figure 8:
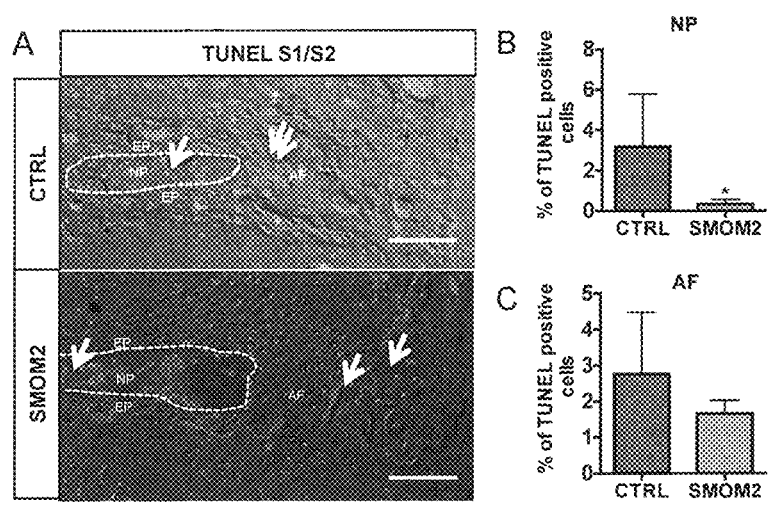

FIG. 8. Activation of HH signaling by SmoM2 in the NP cells reduces cell death in sacral disc. (A) Representative image of TUNEL staining (white arrows) on S1/S2 discs from R26$^{LSL-SmoM2-YFP/LSL-SmoM2-YFP}$ control (CTRL) and CK19$^{CreERT2/+}$; R26L$^{SL-SmoM2-YFP/LSLSmoM2-YFP}$ (SmoM2) littermates. Quantification of the percentage of TUNEL+ cells in NP (B) and AF (C) is determined over the total number of cells in each region counted using DAPI. Mean±S.D. N=6 in each group by combining data from two independent experiments. Unpaired t-test. Scale bars=100 μm.

Figure 9:
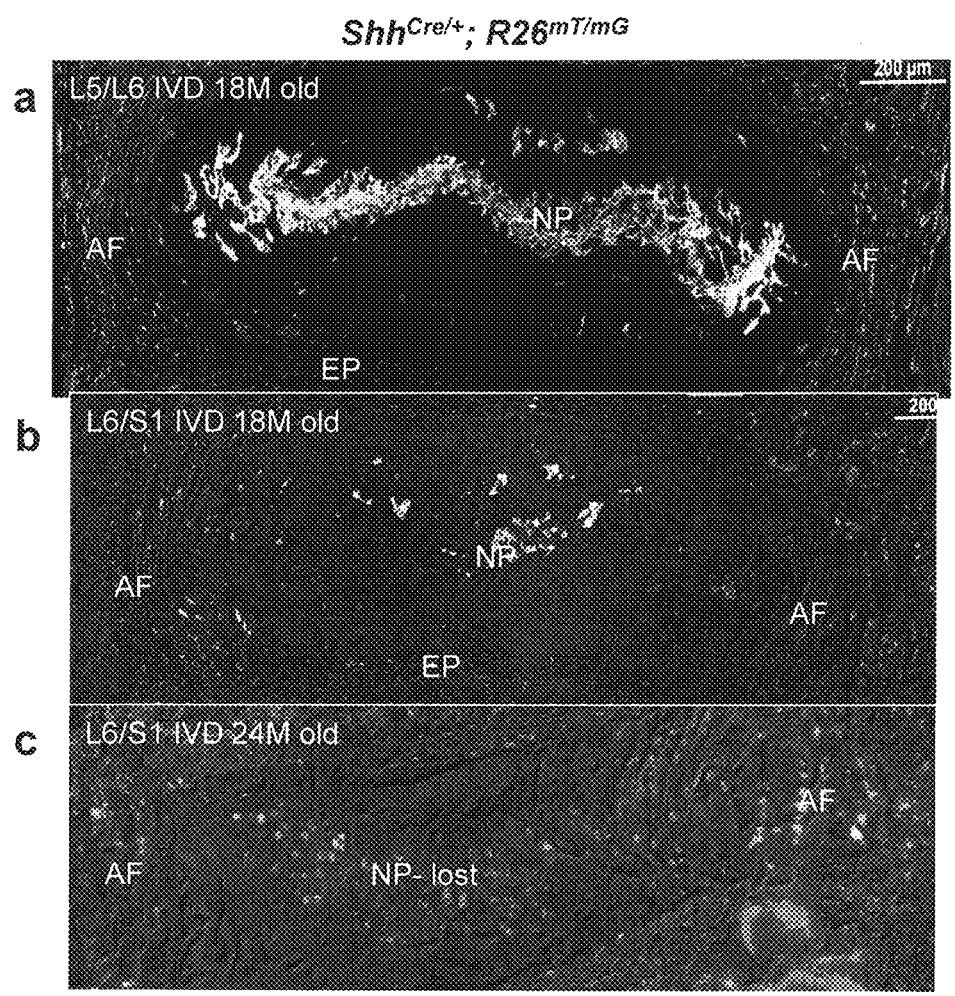

FIG. 9. Mid-coronal sections through 18M (a and b) and 24M (c) old SHH$^{Cre}$; R26$^{mT/mG}$ mice lumbar disc. NP cells (green) that are the source of SHH in the intervertebral disc and spine are lost during normal aging in mouse. Nuclei are counter stained blue. IVD=intervertebral disc, NP=nucleus pulposus, AF=annulus fibrosus, EP=end plate.

Figure 10:
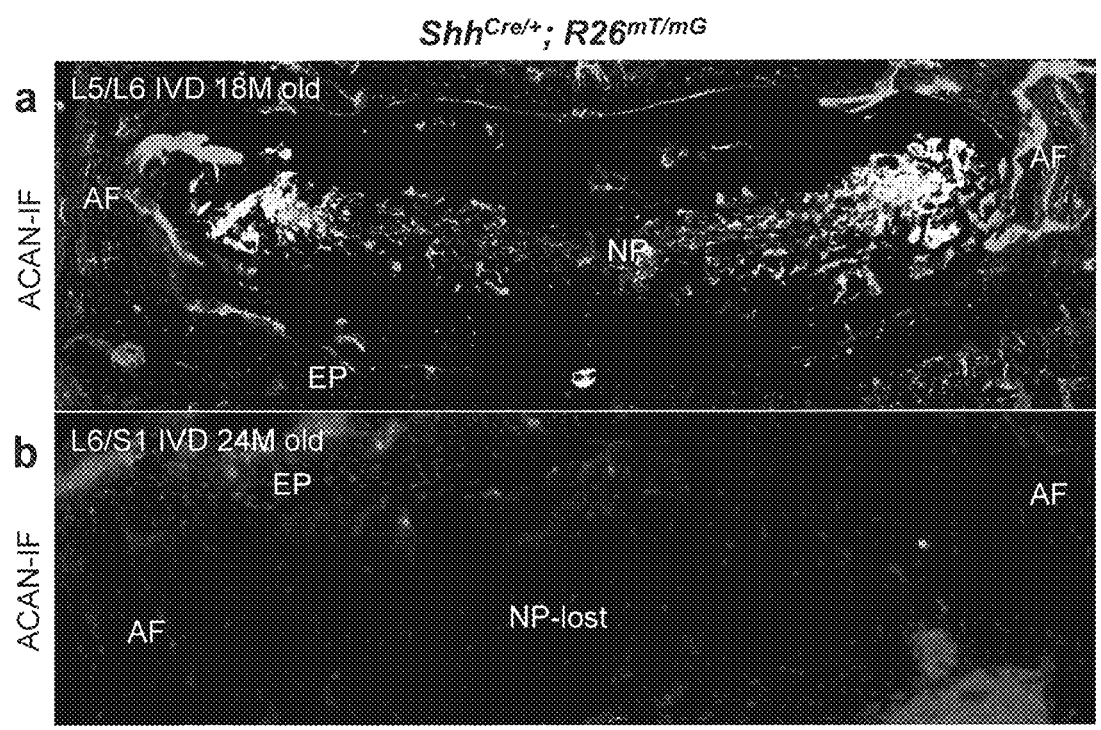

FIG. 10. Mid-coronal sections through 18M (a) and 24M (b) old SHH$^{Cre}$; R26$^{mT/mG}$ mice lumbar disc immunostained for EXM protein aggrecan (ACAN, purple). Loss of NP cells is associated with loss of extracellular matrix in the mouse disc with aging. Nuclei are counter stained blue. IVD=intervertebral disc, NP=nucleus pulposus, AF=annulus fibrosus, EP=end plate, IF=immunofluorescence.

Figure 11:
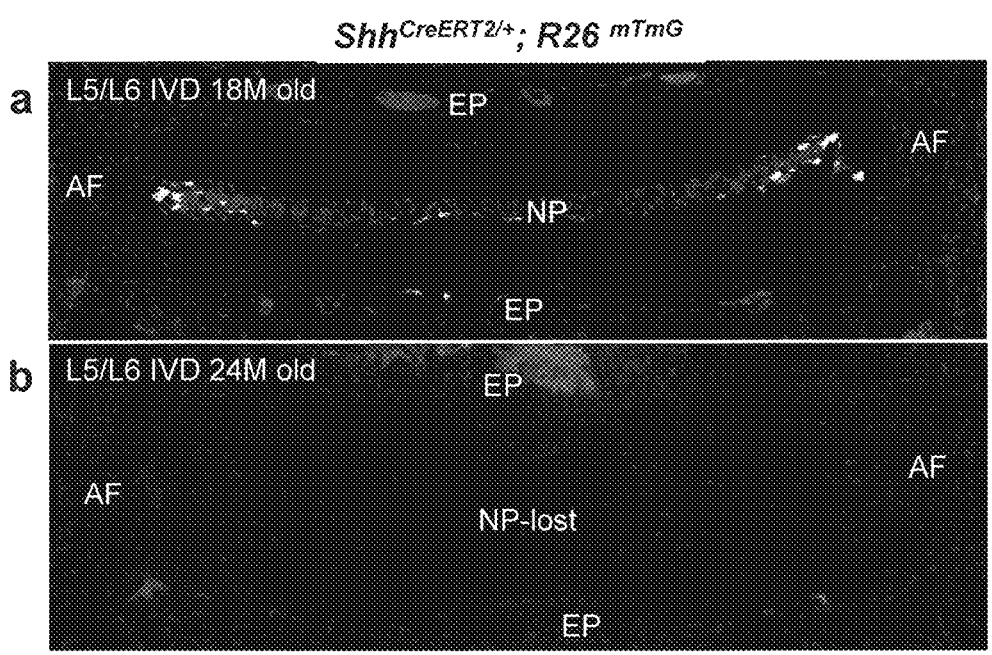

FIG. 11. Mid-coronal sections through 18M (a) and 24M (b) old SHH$^{CreERT2}$; R26$^{mT/mG}$ mice lumbar disc. Mice were gavaged with tamoxifen to induce Cre expression in SHH-expressing cells, and mark them GFP+ (green). The sub-set of NP cells (green) that express SHH in the intervertebral disc are reduced with age, and lost by 24M of age. Nuclei are counter stained blue. NP=nucleus pulposus, AF=annulus fibrosus, EP=end plate.

Figure 12:
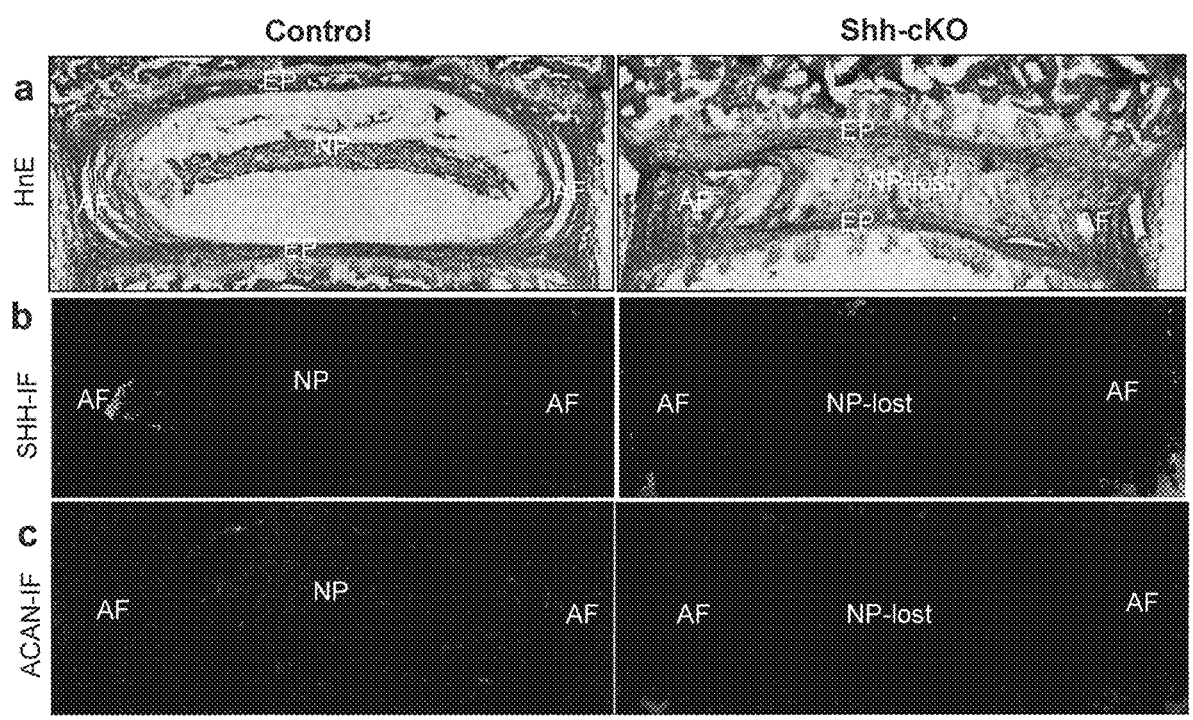

FIG. 12. Conditional targeting of SHH (SHH-cKO) in the NP cells of middle aged mouse causes disc collapse, loss of extracellular matrix (aggrecan-red) and accelerates disc aging within five months following targeting of SHH. Sections are collected in coronal plane. Nuclei are counter stained blue. NP=nucleus pulposus, AF=annulus fibrosus, EP=end plate, IF=immunofluorescence, HnE=hematoxylin and eosin.

Figure 13:
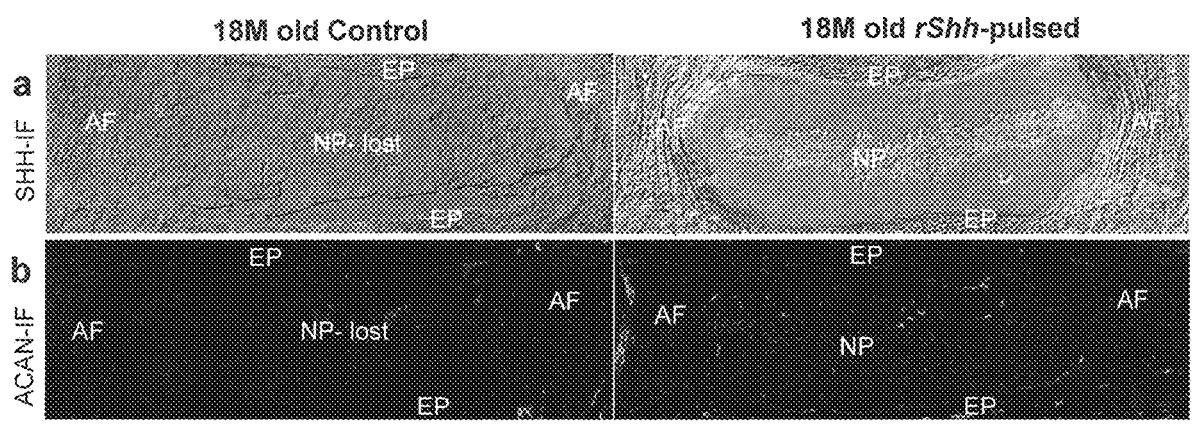

FIG. 13. Transient overexpression of rSHH (rSHH-pulsed) in the NP cells of middle aged mice reactivates the disc and delays aging while the control mouse disc continues to age. The rSHH pulsed mouse disc continue to make more endogenous SHH (red, a) and its target aggrecan (red, b) even five months later. Nuclei are counter stained blue. NP=nucleus pulposus, AF=annulus fibrosus, EP=end plate.

Figure 14:
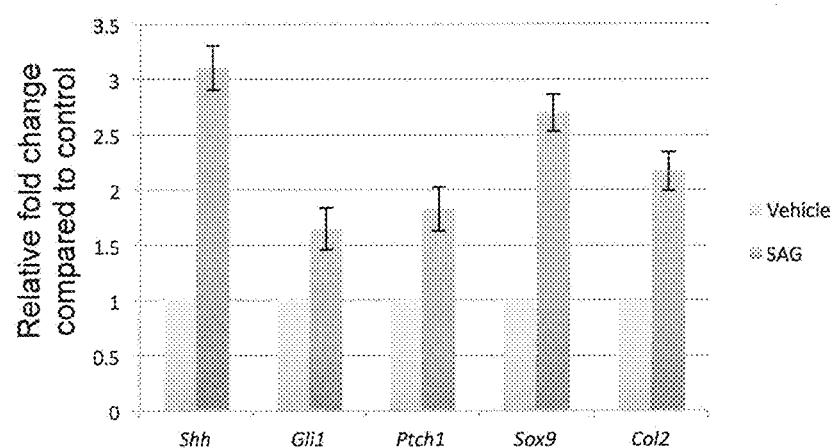

FIG. 14. Real-time RT-qPCR analysis shows up-regulation of SHH and its downstream targets compared to vehicle treated controls in adult mouse intervertebral disc following treatment with SAG (Smoothened Agonist 10 mg/kg body weight), a small molecule agonist of SHH signaling pathway for seven days.

Figure 15:
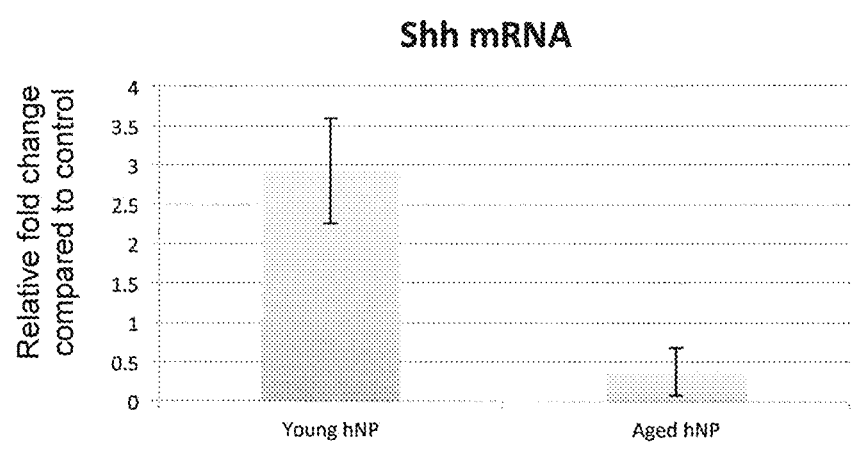

FIG. 15. Real-time RT-qPCR analysis shows mRNA expression of SHH in NP cells collected from patient samples. SHH mRNA expression decreased with age.

Figure 16:
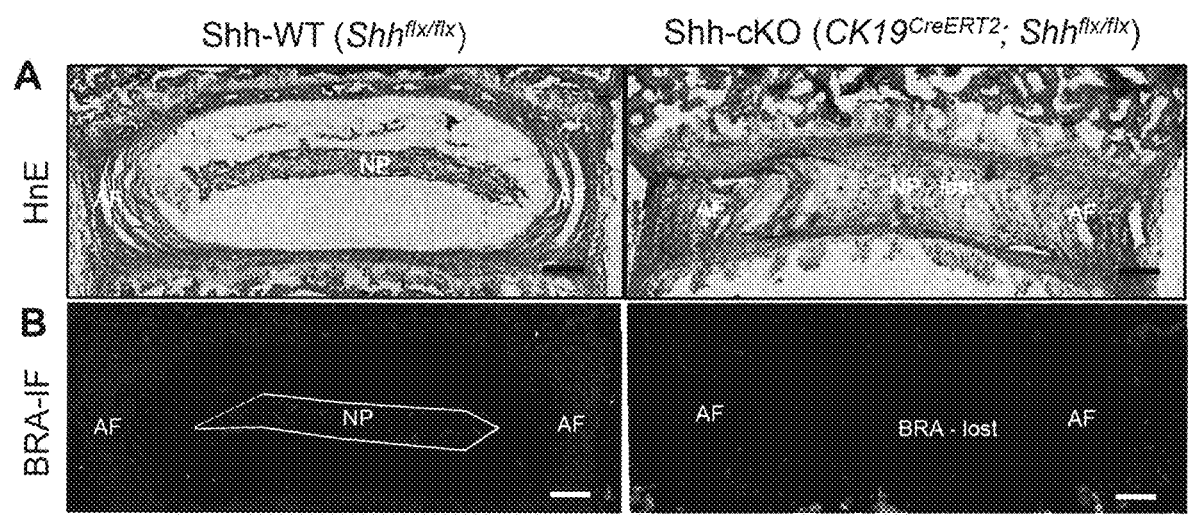

FIG. 16. Conditional targeting of SHH accelerates disc aging and shows a loss of Bra expression. A shows histological changes by HnE staining. B shows immunostaining for Bra (red). Both analyses are on the mid-coronal cryosections of the lumbar disc from tamoxifen treated SHH-WT (SHH$^{flx/flx}$) and SHH-cKO (CK19$^{CreERT2/+}$; SHH$^{flx/flx}$) mice. In B, nuclei are counterstained blue with DAPI. Scale bar=100 μm, n=3 of both males and females.

Figure 17:
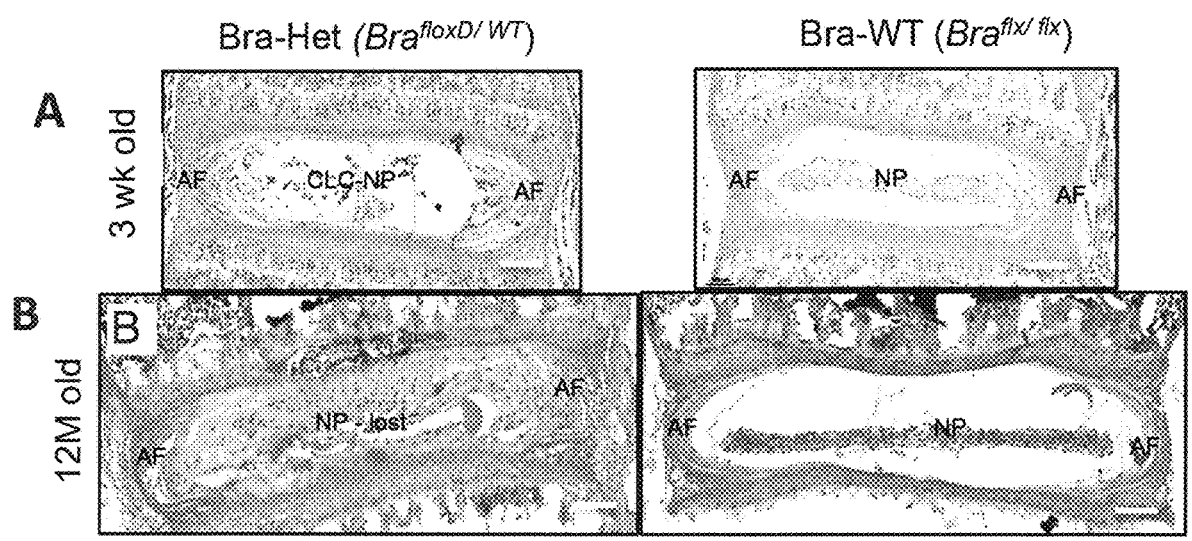

FIG. 17. HnE stained midcoronal sections of the lumbar discs from Bra$^{FloxD/WT}$ (Bra-HET) and Bra$^{flx/flx}$ (Bra-WT) lines at three weeks (A) and 12 months of age (B). Scale bar=100 μm, n=4 of both males and females.

Figure 18:
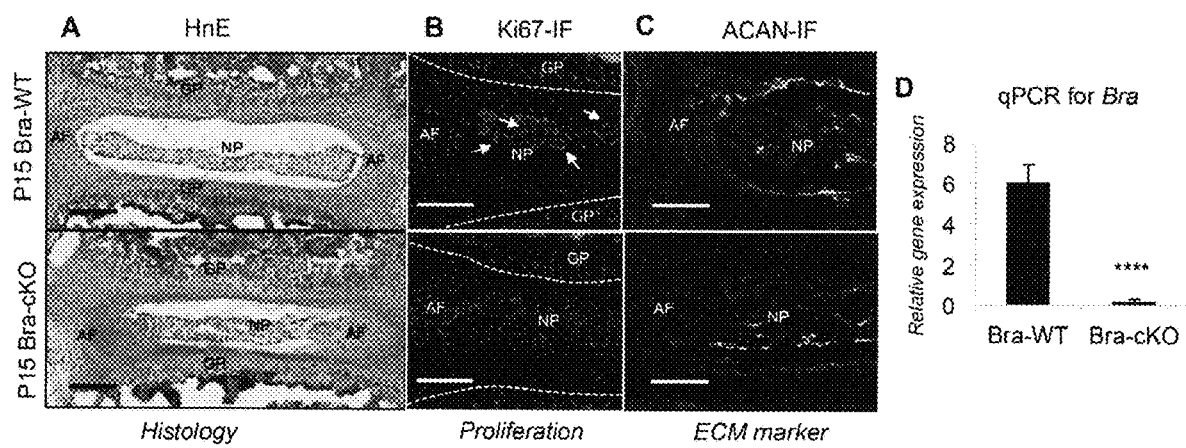

FIG. 18. Conditional targeting of Bra in P4 mice. A shows HnE stained mid-coronal section of tamoxifen treated Bra-WT (Bra$^{flx/flx}$) and Bra-cKO (CK19$^{CreERT2/+}$; Bra$^{flx/flx}$) at P15 age. B shows immunostaining for Ki67 (red), and C shows immunostaining for ACAN (green), an ECM marker. D, shows qPCR analysis for Bra mRNA relative to the reference gene (B2M) in NP cells dissected from Bra-WT and Bra-cKO mice. In B and C nuclei are counterstained blue with DAPI. Scale bar=100 μm. In D, **** is p<0.001. n=3 of both males and females.

DETAILED DESCRIPTION

Examples herein show that human NP cells have decreased expression of SHH as they age. Like SHH expression, Bra expression also decreases with age. Examples herein describe that conditional, constitutive activation of SMO using SmoM2 in a subset of NP cells in a sacral intervertebral disc resulted in an increase in SHH expression and the entire disc showing signs of regeneration (demonstrated by changes in the disc structure, increase in cell number, increase in expression of ECM proteins, and reduction in vascular structures in the disc). Vascularization of the disc is associated with disc degeneration (Kauppila, 1995).

Examples herein also show with fate-mapping studies that during normal aging the SHH-derived as well as the SHH-expressing NP cells are lost, resulting in collapse or fusion of the intervertebral disc and a loss of ECM. By conditionally targeting SHH in middle-aged mice, the collapse and aging of the disc was accelerated as was the loss of ECM proteins, suggesting that degeneration and aging occur due to loss of SHH. Using genetic mouse models that transiently overexpress SHH in the NP cells during the middle age, it was shown that the entire discs remain young and healthier for much longer and continue to make more SHH and SHH downstream targets like ECM proteins. Finally, by intraperitoneal injection of small molecule agonist, SAG, in middle-aged mice, upregulation of SHH signaling targets PTCH1, GLI1 and ECM proteins like SOX9, ACAN, COL2 in the intervertebral disc were observed. Hence, the studies described herein indicate that activation of the SHH signaling pathway using a SHH ligand, or small molecule activator, or manipulating the downstream targets can regenerate the intervertebral disc.

Accordingly, the methods disclosed herein involved the administration of amounts of a SHH signaling pathway activator to subjects having SDD.

I. DEFINITIONS

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a compound" includes a plurality of compounds. Thus, for example, a reference to "a method" includes one or more methods, and/or steps of the type described herein and/or which will become apparent to those persons skilled in the art upon reading this disclosure.

"Ameliorate," "alleviate," "improve," or variants thereof refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with a SHH signaling pathway activator or prior to the subject beginning treatment, where the untreated subjects have, or are subject to developing, the same or similar disease, condition, symptom or the like. Amelioration of a disease, condition, symptom or assay parameter may be determined subjectively or objectively, e.g., self-assessment by a subject(s) (or a caregiver's assessment), by a clinician's assessment or by conducting an appropriate assay or measurement. Amelioration may be transient, prolonged or permanent or it may be variable at relevant times during or after the SHH signaling pathway activator is administered to a subject or is used in an assay or other method described herein or a cited reference, e.g., within timeframes described infra, or about 3 days after the administration or use of a SHH signaling pathway activator to about 7 days, 2 weeks, 28 days, or 1, 3, 6, 9 months or more after a subject(s) has received such treatment. In certain embodiments, the SHH signaling pathway activator is administered chronically.

As used herein, the terms "prevent" of SDD refer to an action, for example, administration of a SHH signaling pathway activator, that occurs before or at about the same time a subject begins to show one or more symptoms of SDD, which inhibits or delays onset or severity of one or more symptoms of the SDD. In some embodiments, a subject may have a genetic predisposition to SDD. In some embodiments, a subject may have a spinal injury, trauma and/or surgery.

The "modulation" of, e.g., a symptom, disc-related measurement or parameter, level or biological activity of a molecule, or the like, refers, for example, that the symptom, parameter, or activity, or the like be detectably increased or decreased. Such increase or decrease may be observed in treated subjects as compared to subjects not treated with SHH signaling pathway activator, where the untreated subjects have, or are subject to developing spinal disc degeneration. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively. Modulation may be transient, prolonged or permanent or it may be variable at relevant times during or after SHH signaling pathway activator is administered to a subject or is used in an assay or other method described herein or a cited reference, e.g., within times described infra, or within 1 week of the administration or use of SHH signaling pathway activator to about 2 weeks, 28 days, 3, 6, 9 months or more after a subject(s) has received SHH signaling pathway activator.

As used herein, "subject" includes an animal, including a person, and having or being at risk for SDD or who could otherwise benefit from the administration of SHH signaling pathway activator as described herein, such as humans.

The language "a therapeutically effective amount" of a compound refers to an amount of SHH signaling pathway activator which is effective, upon single or multiple dose administration to the subject, in treating, managing, reversing, or ameliorating the symptoms of the SDD The language "a prophylactically effective amount" of a compound refers to an amount of SHH signaling pathway activator which is effective, upon single or multiple dose administration to the subject, in preventing or delaying onset of symptoms of SDD.

The term "administration" or "administering" includes routes of introducing SHH signaling pathway activator to a subject to perform its intended function. Examples of routes of administration that may be used include injection (e.g., subcutaneous, epidural, intraperitoneal, or directly into the disc or nucleus pulposus), oral, inhalation, vaginal, rectal, and transdermal. The pharmaceutical preparations may be given by forms suitable for each administration route. For example, these preparations are administered in tablet or capsule form, by injection, inhalation, ointment, or suppository. Administration may also be by injection, infusion or inhalation; topical by lotion, ointment, or patch; and rectal by suppositories. Injection into the disc is preferred.

SHH signaling pathway activator can be administered alone, or in conjunction with either another agent or agents or with a pharmaceutically-acceptable carrier, or both. Administration "in combination with" one or more further therapeutic agents includes simultaneous (concurrent) and consecutive administration in any order.

The phrase "pharmaceutically acceptable" refers to SHH signaling pathway activator as described herein, compositions containing SHH signaling pathway activator, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body.

The term "treat" or "treatment" as used herein is intended to include the reduction, reversal, or amelioration of the progression, severity, and/or duration of a condition or one or more symptoms of SDD.

For example, treating SDD may include an improvement of the following symptoms of SDD, including, for example, a decrease in the degree of pain, an improvement in a flexibility parameter, a decrease in the number of days per week of pain requiring pain relievers, an increase in a disc thickness measurement, attenuation or halting of disc height decline, a decrease in the amount of disc bulging, an improvement in posture, or an improvement in the disc shape.

II. ACTIVE COMPOUNDS

A. SHH Signaling Pathway Activator

In some embodiments, SHH signaling pathway activator can be any small molecule that functions as such. In some embodiments, the SHH signaling pathway activator is SHH, mimics SHH activity, antagonizes Patched activity, or agonizes smoothened activity. In some embodiments, the SHH signaling pathway activator is a downstream effector of the SHH pathway such as smoothened (SMO) and glioma-associated oncogene homolog (GLI) family of zinc finger transcription factors. In an embodiment, the SHH signaling pathway activator is an upregulator of Brachyury (Bra).

In some embodiments, the SHH signaling pathway activator can be SHH or a ligand that mimics its activity ("SHH equivalent"). Examples of SHH agonists have been described in US20100317699A1 and US20060078499A1, all of which are incorporated herein by reference in their entirety. U.S. publication US20100317699A1 describes SHH equivalent compounds having a chemical backbone as shown in Formula (I):

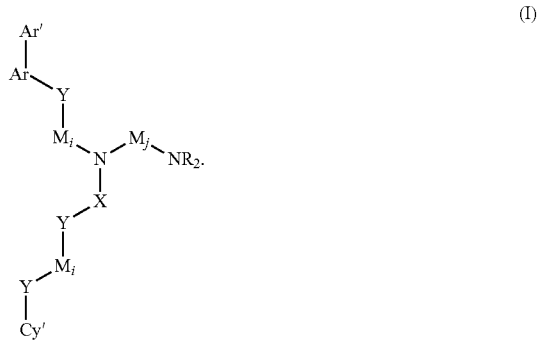

wherein, as valence and stability permit, Ar and Ar' independently represent substituted or unsubstituted aryl or heteroaryl rings; Y, independently for each occurrence, is absent or represent s-N(R)—, —O—, —S—, or —Se—; X is selected from —C(=O)—, —C(=S)—, —S(O2)-, —S(O)—, —P(=O)(OR)—, and a methylene group optionally substituted with 1-2 groups such as lower alkyl, alkenyl, or alkynyl groups; M represents, independently for each occurrence, a substituted or un-substituted methylene group, such a s-CH2-, —CHF—, —CHOH—, —CH(Me)-, —C(=O)—, etc., or two M taken together represent substituted or unsubstituted ethene or ethyne, wherein some or all occurrences of M in Mj form all or part of a cyclic structure; R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N; Cy' represents a substituted or unsubstituted aryl, heterocyclyl, heteroaryl, or cycloalkyl, including polycyclic groups; j represents, independently for each occurrence, an integer from 0 to 10, preferably from 2 to 7; and i represents, independently for each occurrence, an integer from 0 to 5, preferably from 0 to 2.

In certain embodiments, M represents, independently for each occurrence, a substituted or unsubstituted methylene group, such as —CH2-, —CHF—, —CHOH—, —CH(Me)-, —C(=O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent M, if i=0 would result in two occurrences of Y being directly attached, or an occurrence of Y being directly attached to N or NR$_2$.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, X is selected from —C(O)—, —C(=S)—, and —S(O$_2$)—.

In certain embodiments, R represents H or lower alkyl, e.g., H or Me.

In certain embodiments, NR$_2$ represents a primary amine or a secondary or tertiary amine substituted with one or two lower alkyl groups, aryl groups, or aralkyl groups, respectively, preferably a primary amine or secondary amine.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein p and n, individually for each occurrence, represent integers from 0 to 10, preferably from 0 to 5.

A specific embodiment comprises the following structure:

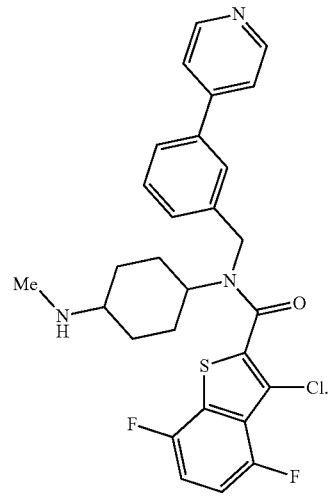 [SMILES: CNC1CCC(N(Cc2cccc(-c3ccncc3)c2)C(=O)c2sc3c(F)ccc(F)c3c2Cl)CC1]

U.S. publication US20060078499A1 describes SHH agonist compounds with the following structure:

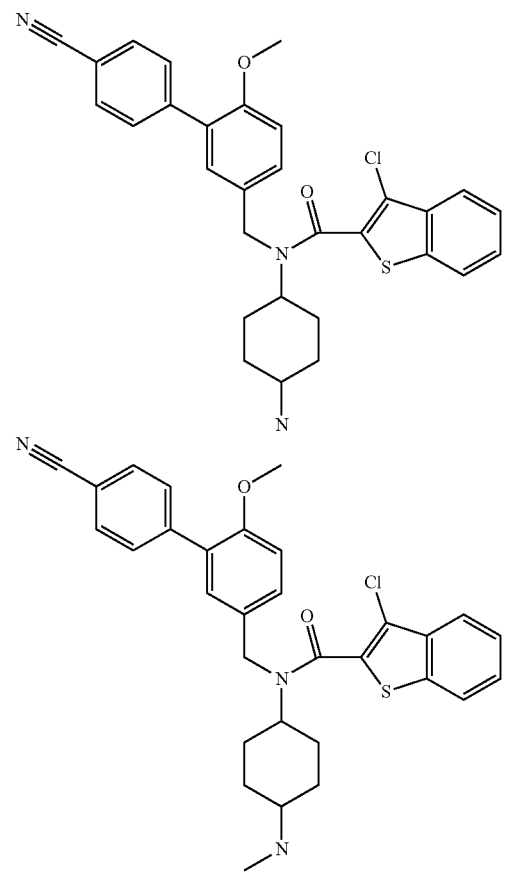

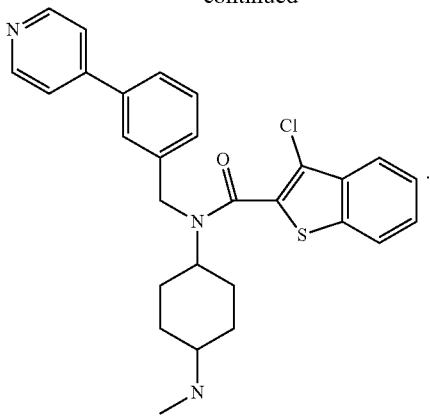

Derivatives of the above structure are also described agonists that can be used in embodiments described herein. The general formula for such derivatives is as follows:

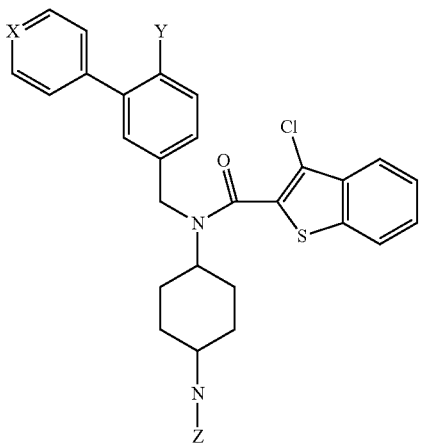

Where X=C or N=C—(CH), C, where 0</=a</=5; Y=R or —O—(CH), CH, where 0</=b</=5; Z=H, CH or CH(CH), where 0</=c</=5.

In an embodiment, the SHH signaling pathway activator is a smoothened agonist. Examples of a smoothened agonist include SAG, purmorphamine, and GSA-10. Examples of smoothened agonist have also been described in WO2011109711A1 (glucocorticoid compounds), all of which is incorporated herein by reference in its entirety. PCT publication WO2011109711A1 describes glucocorticoid compounds having a chemical backbone as follows:

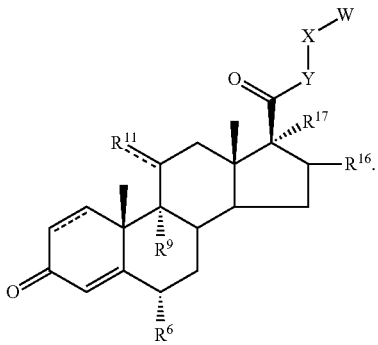

wherein each — independently represents the presence or absence of a bond; $R^6$ is selected from H and halo; $R^9$ is selected from H and halo; $R^{11}$ is selected from H, hydroxy, oxo and halo; $R^{16}$ is selected from alkyl, —OR', —SR\—N(R')_2, —NH—C(O)R" and —NR—S(O)_n—R", or may be taken together with $R1^7$ to form a ring; $R1^7$ is selected from hydroxy and —OC(Z)R", or may be taken together with $R1^6$ to form a ring; Y is selected from a bond, O and S; X is selected from a bond and $CH_2$; W is selected from alkyl, hydroxy, halo and —OC(O)R"; each R' is independently H, alkyl, aryl, heterocyclyl or heteroaryl; each R" is independently alkyl; Z is O or S; and n is 1 or 2; wherein when $R1^6$ and $R1^7$ are taken together to form a ring, they together form the group —O—C($R^a$)_2—O—, wherein each $R^a$ is independently alkyl or two $R^a$ are taken together to form a ring.

In some embodiments, in the compound of formula (I), $R^6$ is selected from H and halo; $R^9$ is halo; $R^{11}$ is selected from hydroxy and oxo; $R^{16}$ is alkyl, or may be taken together with $R^{17}$ to form a ring; $R^{17}$ is selected from hydroxy and —OC(O)R", or may be taken together with $R^{16}$ to form a ring.

In some embodiments, $R^6$ is hydrogen. In some embodiments, $R^6$ is halo (e.g., fluoro). In some embodiments, $R^9$ is halo (e.g., fluoro). In some embodiments, $R^{11}$ is hydroxy. In some embodiments, $R^{11}$ is oxo. In some embodiments, $R^6$ is alkyl (e.g., methyl). In some embodiments, $R^{17}$ is hydroxy. In some embodiments, $R^7$ is —OC(O)CH_2CH_3. In some embodiments, $R^{16}$ and $R^{17}$ are taken together to form a ring; for example, $R^{16}$ and $R^{17}$ may together form a group selected from -OO—C(CH_3)_2—O— and

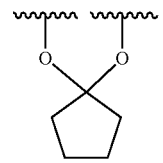 [SMILES: *OC1(O*)CCCC1]

in some embodiments, the group —Y—X—W is selected from the group consisting of —CH_2—Cl, —S—CH_2—F, —CH_2—OAc, —CH_2—OH, —CH_3 and —CH_2—I.

In an embodiment, the SHH signaling pathway activator can be an oxysterol. Examples of suitable oxysterols have been described in U.S. Pat. No. 9,526,737B2, all of which is incorporated herein by reference in its entirety. U.S. Pat. No. 9,526,737B2 describes oxysterols having a chemical backbone as follows:

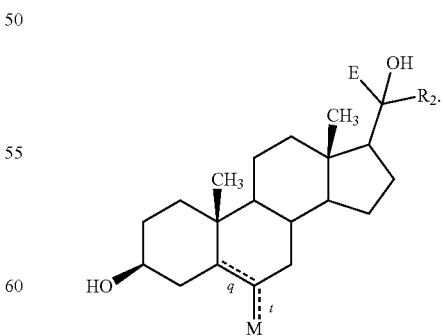

wherein q can be a single bond or a double bond; and t can be a single bond or a double bond. At least one of q and t can be a single bond. M can be hydrogen (—H), hydroxy (OH), formoxy (—O(C═O)H), acetoxy (—O(C═O)CH_3), acyloxy (—O(C=O)-alkyl), oxygen (=O), alkoxy (—O-alkyl), sulfhydryl (—SH), alkylthio (—S-alkyl), amino (—NH₂), methylamino (—NHCH₃), alkylamino (—NH-alkyl), formamido (—NH(C=O)H), acetamido (—NH(C=O)CH₃), and alkylamido (—NH(C=O)-alkyl), with alkyl of from 1 to 6 carbons. When M is oxygen, then t can be a double bond and q can be a single bond. When M is hydrogen, hydroxy, or acetoxy, then t can be a single bond. E can be alkyl of from 1 to 6 carbons, for example, methyl. R₂ can be alkane of from 1 to 6 carbons, alkene of from 2 to 6 carbons, alkyne of from 2 to 6 carbons, aralkyl of from 4 to 12 carbons, aralkene from 5 to 12 carbons, aralkyne of from 5 to 12 carbons, halogen-substituted aralkyl of from 4 to 12 carbons, halogen-substituted aralkene from 5 to 12 carbons, halogen-substituted aralkyne of from 5 to 12 carbons, alkyl-substituted aralkyl of from 5 to 18 carbons, alkyl-substituted aralkene from 6 to 18 carbons, alkyl-substituted aralkyne of from 6 to 18 carbons, hydroxy-substituted alkyl of from 1 to 6 carbons, hydroxy-substituted alkene of from 2 to 6 carbons, or hydroxy-substituted alkyne of from 2 to 6 carbons. For example, R₂ can be phenalkane of from 7 to 12 carbons, halogen-substituted phenalkane of from 7 to 12 carbons, phenyl-substituted alkene of from 8 to 12 carbons, phenyl-substituted alkyne of from 8 to 12 carbons, thiophene-substituted alkyl of from 5 to 11 carbons, thiophene-substituted alkene of from 6 to 11 carbons, or thiophene-substituted alkyne of from 6 to 11 carbons.

In an embodiment, the compound has an activity when contacted with a human or animal cell of stimulating osteoblastic differentiation, inhibiting adipocyte differentiation, stimulating cartilage formation, stimulating hair growth, and/or stimulating angiogenesis.

When q is a double bond, M is hydrogen, and E is methyl, then R₂ can be other than ethyl, n-propyl, 4-methylpentyl, 4-methyl-3-pentenyl, 4-methyl-4-pentenyl, and 1-hydroxy methylpentyl. For example, when q is a double bond and M is hydrogen, then R₂ can be other than methylbenzyl.

When q is a single bond, M is hydrogen, and E is methyl, then R₂ can be other than 4-methylpentyl, vinyl, 1-hydroxy-4-methylpentyl, 3-hydroxy-3-methylbutyl, 4-hydroxy-4-methylpentyl, 1,4-dihydroxy-4-methylpentyl, 1,5-dihydroxy-4-methylpentyl, and 2-phenylethenyl. For example, when q is a single bond, M is hydroxy, and E is methyl, then R₂ can be other than 4-methyl-pentyl and 4-methyl-3-pentenyl. For example, when q is a double bond, M is hydrogen, and E is methyl, then R₂ can be other than ethyl, n-propyl, n-butyl, n-pentyl, t-butyl, 1-methylpropyl, 3-methylbutyl, 3-methylpentyl, 4-methylpentyl, vinyl, allyl, 1-propenyl, 4-methyl-3-pentenyl, 4-methyl-4-pentenyl, 3-hydroxy-3-methylbutyl, 4-hydroxy-3-methylbutyl, 1-hydroxy-4-methylpentyl, 4-hydroxy-4-methylpentyl, 4-hydroxy-4-methyl-1-pentenyl, 4-hydroxy-4-methyl-2-pentenyl, 1,4-dihydroxy-4-methylpentyl, and 1-(2-pyridinyl)ethyl. For example, when q is a double bond, M is hydrogen, and E is 4-methylpentyl, then R₂ can be other than hydroxymethyl. For example, when q is a double bond and M is hydrogen, then R₂ can be other than methylbenzyl. For example, when t is a double bond, M is oxygen, and E is methyl, then R₂ can be other than 4-methyl-pentyl and 1-hydroxy-4-methylpentyl.

When q is a double bond, M is hydrogen, and R₂ is alkane or alkene, then R₂ can be

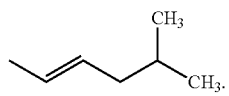

M can be hydroxy and R₂ can include

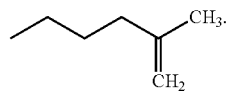

III. METHODS OF TREATMENT

Provided herein are methods of treating, preventing, reversing, reducing, or alleviating one or more symptoms caused by a SDD comprising administering to a subject in need thereof a therapeutically effective amount of an SHH signaling pathway activator. In particular embodiments, the SHH signaling pathway activator is SAG. The subject is preferably a human. In other embodiments, the subject is mammal, such as a horse, cow, camel, dog, or cat.

The methods of treatment provided herein treat, reduce, prevent or alleviate pain associated with SDD. SDD that have been identified as associated with pain and can be treated with a SHH signaling pathway activator.

The methods of treatment provided herein repair or improve the function of an intervertebral disc. In particular embodiments, the subject has a spinal injury and had a surgery on an area near or involving the spine. In particular embodiments, the subject has an injury to a disc or is suffering from inflammation that is having a detrimental or damaging effect on a disc.

In one embodiment, treating SDD includes an improvement of the following symptoms of SDD, including, for example, pain, inflammation, and one or more flexibility parameters (e.g., neutral zone, range of motion and neutral zone ratio). This decrease or increase may be measured from a baseline. The baseline may be determined in the days prior to treatment with SHH signaling pathway activator.

In one embodiment, treating SDD includes an improvement of a measurement of a magnetic resonance imaging (MRI)-based, X-ray-based, or CT-based disc and vertebral measurement used to measure degeneration as compared with a measurement prior to treatment. Such measurements include increasing the disc thickness and/or density, reducing axial deformation of the disc (e.g., (1) intact, (2) bulge, (3) protrusion, (4) extrusion and/or (5) sequestration), reduction in amount of size of tears or ruptures; or an improvement in the shape of the nucleus (e.g., by (1) round/oval, (2) extension into inner annulus, (3) extension into outer annulus and/or (4) extension beyond outer annulus).

In certain embodiments, the SHH signaling pathway activator is administered until symptoms of SDD are ameliorated and then SHH signaling pathway activator is discontinued. Since SDD may be likely to recur once treatment ceases, the SHH signaling pathway activator may be administered chronically on an intermittent basis at a prophylactically effective amount to prevent, delay or attenuate a return of degeneration.

As will be readily apparent to one skilled in the art, the useful in vivo dosage to be administered and the particular mode of administration may vary depending upon the age, weight, amount of degeneration, the type of mammalian species treated, the particular actives employed, and/or the mode of administration. The determination of effective dosage levels, that is the dosage levels necessary to achieve the desired result, can be accomplished by one skilled in the art using routine pharmacological methods and in consultation with the data presented herein and the potency and half-life of the particular active being used.

A dose of a SHH signaling pathway activator may be administered, for example, once a day, once every other day, once a week, every other week ("biweekly"), once a month, every other month ("bimonthly"), every 3 months, every four months, every 6 months, or once a year. SHH signaling pathway activator is SAG and may be administered in doses, for example of from about between 5 mg to about 3000 mg per dose, preferably SHH signaling pathway activator is administered from between about 100 mg to about 1000 mg per dose; or from about 1000 mg to about 2000 mg per dose. In another embodiment, SHH signaling pathway activator is administered between 50 mg to about 500 mg per dose depending of symptoms. In embodiments, the SHH signaling pathway activator is formulated in a liquid, injectable form. In other embodiments, the SHH signaling pathway activator is an oral dosage form.

In certain embodiments, particularly for oral or other non-localized administration, SHH signaling pathway activator is SAG and administered at a dose from 2 to 30 mg/kg, specifically about 2 mg/kg, 5 mg/kg, 10 mg/kg, 15 mg/kg, 20 mg/kg, 25 mg/kg or 30 mg/kg per dose. The SHH signaling pathway activator may be formulated in a solid or liquid oral dosage form.

In other embodiments, the subject is treated with SHH signaling pathway activator for 2, 4, 6, 8, 10, 12, 14, 16, 18, 20, 22, 24, 26 or more weeks or 26 or more weeks. In preferred embodiments, SHH signaling pathway activator is administered chronically. Length of treatment may vary depending on the severity of the degeneration.

In one aspect, provided herein are methods of increasing the thickness of a spinal disc or reducing the extent of disc bulging by administering a composition comprising the SHH signaling pathway activator at an effective amount to the subject.

In another aspect, provided herein are methods for inhibiting the onset of SDD by administering to a subject in need thereof a prophylactically effective amount of SHH signaling pathway activator.

In certain embodiments, the subject is administered SHH signaling pathway activator for treatment of SDD in combination a Wnt signaling pathway activator. In certain embodiments, the subject is administered SHH signaling pathway activator wherein the SHH signaling pathway activator is independent of the Wnt signaling pathway.

IV. PHARMACEUTICAL PREPARATIONS

Also provided herein are pharmaceutical compositions, comprising an effective amount of a SHH signaling pathway activator described herein and a pharmaceutically acceptable carrier. In a further embodiment, the effective amount is effective to treat, reverse, prevent or ameliorate SDD or one or more symptoms thereof. In a further embodiment, the effective amount is effective to repair or improve the function of an intervertebral disc.

One embodiment includes pharmaceutical compositions comprising SHH signaling pathway activator and a pharmaceutically acceptable carrier. In some embodiments, the pharmaceutical composition is an injectable form, e.g., a form suitable for injection into the epidural space. In some embodiments, the pharmaceutical composition is an oral dosage form, such as a tablet or capsule. In some embodiments, the pharmaceutical composition is for topical use.

In certain embodiments, pharmaceutical compositions can comprise a Wnt signaling pathway activator in addition to and distinct from a SHH signaling pathway activator. In other embodiments, pharmaceutical compositions comprises a SHH signaling pathway activator consisting only a SHH signaling pathway activator that are independent of the Wnt signaling pathway.

The pharmaceutical compositions described herein may further comprise excipients, for example, one or more of a stabilizing agent, preserving agent, diluting agent, viscosity modifying agent, binding agent, lubricating agent, disintegrating agent, coloring agent, flavoring agent or sweetening agent. Compositions may be formulated for selected coated and uncoated tablets, hard and soft gelatin capsules, sugar-coated pills, lozenges, wafer sheets, pellets and powders in sealed packet. Compositions may be formulated for topical use, for example, patches, ointments, pomades, creams, gels and lotions.

In certain embodiments, the pharmaceutical compositions may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular, epidural, intraperitoneal, or intravenous injection as, for example, a sterile solution or suspension; (3) topical application, for example, as a cream, ointment, patch, or spray applied to the skin; (4) intravaginally or intrarectally, for example, as a pessary, cream or foam; or (5) aerosol, for example, as an aqueous aerosol, liposomal preparation or solid particles containing the compound.

A pharmaceutical carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing SHH signaling pathway activator include those suitable for oral, nasal, topical (including buccal and sublingual), rectal, vaginal, aerosol epidural, and/or parenteral administration. The compositions may conveniently be presented in unit dosage form and may be prepared by any methods known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.01% to about 99% w/w of active ingredient, for example, from about 5% to about 70% w/w, or from about 10% to about 30% w/w.

Liquid dosage forms for injectable administration of SHH signaling pathway activator may include, for example, pharmaceutically-acceptable emulsions, microemulsions, solutions, and suspensions. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to SHH signaling pathway activator may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Dosage forms for the topical or transdermal administration of SHH signaling pathway activator can include, for example, powders, sprays, ointments, pastes, creams, lotions, gels, solutions, patches and inhalants. The ointments, pastes, creams and gels may contain, in addition to SHH signaling pathway activator, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a SHH signaling pathway activator, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Examples of suitable aqueous and non-aqueous carriers which may be employed in the pharmaceutical compositions can include, for example, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In one embodiment, SHH signaling pathway activator is enteric coated so as to protect it from degradation by the acidic conditions of the stomach and/or from interactions with proteins, such as pepsin, present in the stomach, e.g., an enteric protected formulation. In a specific embodiment, SHH signaling pathway activator is in tablet form. In yet another embodiment, the tablet is enteric coated, e.g., Eudragit®. In one embodiment, SHH signaling pathway activator is formulated as an enteric coated bead or granule in an enteric coated capsule shell. In another embodiment, SHH signaling pathway activator is formulated in a delayed release composition.

Regardless of the route of administration selected, SHH signaling pathway activator is formulated into pharmaceutically-acceptable dosage forms by methods known to those of skill in the art.

Also provided herein are pharmaceutical formulations of SHH signaling pathway activator comprising the composition along with a pharmaceutically acceptable carrier, at a dose which is therapeutically effective at treating SDD or a symptom thereof.

In combination therapy treatment, both the compounds and the other drug agent(s) are administered to mammals (e.g., humans, male or female) by methods known in the art. The agents may be administered in a single dosage form or in multiple dosage forms. Notwithstanding, a dose amount is the amount administered at a particular instance in time.

V. KITS

Kits are also provided herein, for example, kits for treating SDD or one or more symptoms associated with SDD in a subject. The kits may contain, for example, SHH signaling pathway activator or a pharmaceutical composition comprising SHH signaling pathway activator and instructions for use. The kit may comprise a vial with the pharmaceutical composition comprising SHH signaling pathway activator. The kit may comprise a pre-filled syringe. The instructions for use may contain prescribing information, dosage information, storage information, and the like.

Label instructions include, for example, instructions to take the SHH signaling pathway activator by injection. The instructions could also instruct, for example, take a dosage of the SHH signaling pathway activator daily, every other day, or twice a day until resolution of symptoms.

VI. EXAMPLES

Formation of Mouse Sacrum

Most mice strains have seven cervical, thirteen thoracic, five to six lumbar, and four sacral vertebrae (A. and Michie, 1958; Wellik, 2007). To determine the time line of sacrum formation in mouse, the sacral discs (S1/S2, S2/S3, S3/S4) from FVB mice ranging from neonatal (postnatal day four, P4), rapid growth phase (four week), end of longitudinal growth period (twelve and fourteen weeks), and mid-age (one-year old) were compared by X-ray (FIG. 1B), and histomorphometric analysis was carried out on hematoxylin and eosin (Hand E) stained midcoronal sections (FIG. 1A, C-F). All sacral discs had normal histology at P4 with reticular NP cells and organized layers of AF (FIG. 1A). At four weeks, all sacral discs continued to have reticular NP, while the AF was disorganized in the two most cranial sacral discs (S1/S2 and S2/S3). By 12 to 14 weeks of age, the NP cells had collapsed in the two cranial discs, and the disc height and NP spaces were dramatically reduced compared to S3/S4 (compare S1/S2 with S3/S4 in FIGS. 1A, D and E). The AF of these two discs appeared more disorganized, had no detectable layers, and contained structures that appeared like vascular bodies, which are known to appear during age-related disc degeneration (Kauppila, 1995; Nerlich et al., 2007). This was confirmed, and quantitated for each disc by immunostaining for the endothelial cell marker CD31

(PECAM-1, FIGS. 1H and I). Immunofluorescence confirmed the presence of vascular bodies in the AF as early as four weeks of age.

In contrast to the two cranial sacral discs, the S3/S4 disc maintained a normal histology, and did not fuse at any of the stages studied. The only change observed was the vascularization of the EP starting at 12 weeks of age (FIG. 1). X-rays showed a progressive decline in the spaces (green arrow heads) between the S1/S2, and S2/S3 discs four weeks onwards, while the S3/S4 disc space was maintained at all stages that were analyzed (FIG. 1B). Histomorphometric analysis showed a similar pattern with rapid growth in height of S3/S4 discs from P4 to four week of age, minor decline by 12-14 weeks of age and were maintained thereafter (p=0.0013), while the height of the S1/S2 and S2/S3 disc remained constant until 14 weeks of age, and reduced thereafter (p=0.9064 and 0.0021 respectively) (FIG. 1D). A similar pattern in the NP area and the number of NP cells was observed, with a significant increase from P4 to four week followed by significant reduction at 14 weeks, which continued to decline by one-year of age (FIGS. 1F and G). By one-year, there were very few NP cells in the S1/S2 and S2/S3 discs, and they were all round and clumped together (FIG. 1A). To confirm that the round and clumped cells in the upper two sacral discs of a mid-aged mouse were NP cells, the mid-coronal sections of S2/S3 discs from 18 month old $SHH^{GFPcre/+}$, $-R26^{mTmG}$ line were analyzed. This test showed the center of the disc green, confirming that its origin was from the earlier NP cells. An increase in the number of NP cells from P4 to four week of age is associated with high proliferation rate of these cells as seen by the percentage of Ki67+ immunostained NP cells at P4, which decreased by four weeks of age more dramatically in S1/S2 and S2/S3 discs than in S3/S4 (FIGS. 2A and B). No cell proliferation was seen by 12 weeks of age in all sacral discs. TUNEL assay showed an increase in percentage of positive cells in the S1/S2 and S2/S3 discs from four weeks of age (FIGS. 2C and D), showing that the decreased number of NP cells is a result of cell death.

Loss of SHH and its Targets is Associated with the Collapse of the Sacral Disc

SHH signaling by the NP cells is required for postnatal growth and differentiation of the disc, and decreases with age (Dahia et al., 2012; Dahia et al., 2009a; Winkler et al., 2014). To determine whether collapse of the S1 to S3 sacral discs is associated with the loss of SHH signaling (or loss of response to SHH signaling), immunostaining for SHH in S1/S2, S2/S3 and S3/S4 discs during growth and differentiation were carried out. FIG. 3A shows dramatic decrease in SHH expression four weeks onwards in S1/S2, but its expression decreases much more slowly in S3/S4, which maintains its normal structure for longer. This result is shown also for the SHH transcriptional targets CK19 and Bra. The expression of CK19 and Bra was reduced in the S1/S2 discs four weeks onwards compared to the S3/S4 disc where their expression was detectable until one year of age (FIGS. 3B and C), corresponding to that of SHH. The immunostaining data for S2/S3 discs is not shown, as the results were similar to S1/S2 discs. Quantification of immunofluorescence intensities for SHH, CK19 and Bra in all the three sacral discs is provided in FIG. 4A-C.

ECM plays an important role in the maintenance of the structure and function of the notochord [reviewed by (Stemple, 2005)] and the discs [reviewed by (Sivan et al., 2014; Urban and Roberts, 2003)]. The NP is rich in proteoglycans and GAGs (Antoniou et al., 1996), while the AF is relatively rich in collagens, which form its fibrils [reviewed by (Urban and Roberts, 2003)]. SHH regulates the expression and synthesis of ECM markers both in the NP and in AF during postnatal development, and the expression of these markers is reduced with age (Dahia et al., 2012; Winkler et al., 2014). The expression of the ECM markers, Chondroitin sulfate (CHSO4) and Collagen 1 (COL1), was analyzed by immunofluorescence in all sacral discs during postnatal growth and differentiation. The expression of CHSO4 and COL1 was decreased in the AF in S1/S2 discs by 12 to 14 weeks of age, but continued to be present until one year of age at the S3/S4 level (FIGS. 5A and B). The expression pattern of both CHSO4 and COL1 was very similar in S2/S3 to that in S1/S2, and hence is not shown. Quantification of immunofluorescence intensities for CHSO4 and COL1 for all the three sacral discs is provided in FIGS. 6A and B. Down-regulation of the ECM markers was observed not only in the NP cells which are the SHH-expressing, but also in the surrounding AF of the sacral discs with age, indicating that they respond to SHH produced by the NP cells.

Conditional Activation of 1111 Pathway in the NP Cells can Re-Awaken the Sacral Disc This test examined whether the collapse of sacral discs can be reversed by reactivation of SHH signaling. This was done at 12 weeks of age when the expression of SHH in the S1/S2 disc is already reduced, and the NP cells have begun to lose their reticular phenotype, becoming rounder and clumped together. For this study we used the $CK19^{CreERT2}$ driver line. First, the amount of cells expressing CK19 and capable of undergoing recombination was examined by administering two doses of tamoxifen to four-month old $CK19^{CreERJ+}$, $-R26^{mTmG}$ and analyzing mid-coronal sections through the most cranial sacral discs. FIG. 7A shows that few cells express CK19 by this age in the S2/S3 discs (shown by white arrow heads).

Next, $CK19^{CreERT2/+}$ was crossed with $R26^{LSL-SmoM2-YFPILSLSmoM2-YFP}$ to generate $CK19^{creERT2/+}$; $R26^{LSL-SmoM2-YFPI+}$ (SmoM2) and $R26^{LSL-SmoM2-YFPI+}$ (WT) alleles. Twelve week old littermates were treated with two doses of tamoxifen to induce expression of the constitutively active form of SMO (caSmo) commonly known as SmoM2 (Jeong et al., 2004) even in the absence of SHH ligand. This recombination will occur only in the sub-set of NP cells that express CK19 (shown in FIG. 7A). The mice were euthanized and the sacral spines collected two weeks after the last tamoxifen dose (FIG. 7B). Results were compared with littermate controls. FIG. 7C and FIG. 6 show a dramatic rescue of the histology in SmoM2 group compared to the littermate controls. All the NP cells had become reticular and evenly distributed, and the AF is more organized in the SmoM2 group. Histomorphometric analysis shows quantifiable differences that included improvement in disc height (FIG. 7C), NP area (p=0.0160, FIG. 7D), and an increase in the number of NP cells (p=0.0003) (FIG. 7E) in the SmoM2 group compared to littermate controls. The AF of SmoM2 discs also have more defined layers (FIG. 7F). TUNEL assay shows a significant (p=0.0432) reduction in cell death of NP cells (FIG. 8A-C) following activation of HH signaling in the S1/S2 discs of SmoM2 mice compared to the controls. Interestingly, immunostaining for YFP (fused to SmoM2) showed that over 75% of NP cells were positive (FIGS. 7G and H). Thus, since only a sub-set of NP cells normally expresses $CK19_{CreERT2}$ in the S1/S2 sacral disc at 12 weeks (FIG. 7A), these results suggest an expansion of the SmoM2-expressing NP cells. Furthermore, irrespective of being YFP+, all NP cells in the SmoM2 experimental discs were reticular. Hence, we analyzed the expression of SHH and found it to be higher in the SmoM2 discs (FIGS. 7I and J), supporting the hypothesis that induction of SmoM2 expression stimulates SHH expression by NP cells and the sacral discs then respond to high levels of SHH irrespective of the whether these were the recombined cells expressing SmoM2 allele. This result also explains the rescue in the AF phenotype despite the expression of SmoM2 being driven exclusively in the NP cells. An increase in the downstream targets of SHH: PTCH1, CK19, CHSO4, and COL1 (FIG. 7K-P) was observed in the SmoM2 experimental discs. To determine whether vascularization of the AF in S1/S2 discs after 12 weeks of age (FIGS. 1H and I) occurred as a result of decreased SHH levels, we quantified the number of PECAM-1+ vascular structures in the AF and EP of the experimental SmoM2 discs compared to controls. The results show a significant decrease (p=0.0218) in the PECAM-1+ structures (FIGS. 7Q and R) in the AF of the SmoM2 disc, although no change was observed in the EP. Vascularization of the AF has been described with aging and disc degeneration (Binch et al., 2014; Kauppila, 1995; Melrose et al., 2002; Nerlich et al., 2007), and has been related to loss of ECM, mostly proteoglycans (Johnson et al., 2005; Melrose et al., 2002.

Intervertebral Disc Aging is Associated with Loss of Sill-Derived NP Cells and Sill Expression Previously it has been shown that the entire postnatal NP is derived from SHH-expressing notochordal cells (Choi et al., 2008). To determine the fate of SHH-derived NP cells during aging, a $SHH^{GFPCre/+}$; $R26^{mTmG}$ by crossing $SHH^{tm1(EGFP/cre)Cjt/J}$ (Harfe et al., 2004) with $R26^{tm4(ACTB-tdTomato,-EGFP)Luo}$ ($R26^{mTmG}$) (Muzumdar et al., 2007), where only SHH-derived notochord cells express Cre; fox out membrane localized tdTOMATO (mT), turn "on" membrane localized EGFP (mG) and are marked "green", while the remaining cells continue to express mT and stay "red". Lineage tracing in skeletally mature 18 month-old (18M) $SHH^{GFPCre/+}$; $R26^{mTmG}$ mice show that the entire NP is exclusively composed of SHH-derived cells (SHH+) (FIG. 9a-b). Most strains of mice, including the strains used in this study, have six lumbar vertebrae. The L5/L6 disc at 18M of age maintained a defined structure with reticular NP cells and organized AF layers (FIG. 9a). In contrast, lumbosacral (L6/S1) discs show an aging phenotype with fewer, rounder NP cells and disorganized AF layers which move into the NP space (FIG. 9b). By 24M, no SHH+ green cells are seen in the NP space, the intervertebral disc becomes hypocellular and is collapsed along with reduced disc height (FIG. 9c). Immunostaining for Aggrecan (ACAN) shows loss of ECM associated with the collapse of the disc from 18M to 24M of age (FIGS. 10a and b).

Loss of SHH Expression with Age is Associated with Degeneration and Collapse of the Intervertebral Disc Compared to neonatal mouse NP cells, expression of SHH and its downstream ECM markers are greatly reduced in one year-old mouse discs (Winkler et al., 2014). Thus even at lower levels, SHH can maintain the intervertebral discs and delay aging for another year or so. Whether the reduction in the amount of SHH is due to fewer cells making it, and towards this we analyzed the population of SHH-expressing NP cells at 12M and 24M of age by crossing tamoxifen-inducible SHH driver line $SHH^{CreERT2/+}$ (Harfe et al., 2004) and $R26^{mTmG}$ reporter (Muzumdar et al., 2007) to generate an inducible SHH reporter ($SHH^{CreERT2/WT}$, $R26^{mT/mG}$) line, and collected lumbar spine two days after last tamoxifen administration. At 12M, only a subset of NP cells express SHH, which are located predominantly in the NP periphery and closer to AF and EP (FIG. 11a). These few SHH+NP cells seem sufficient to maintain disc structure, with reticular NP and a well-organized AF. By 24M the collapsed lumbar disc was hypocellular with no remaining SHH+ cells (FIG. 11b). These results suggest that loss of SHH expression with aging results in loss of disc cell number, ECM proteins, and disc height.

Conditional Targeting of SHH in the Adult Mouse NP Cells

To test whether loss of SHH causes disc aging, SHH foxed allele [SHHtm2Amc/J (Lewis et al., 2001)] was crossed with $CK19^{CreERT2/+}$ (Means et al., 2008), and SHH was targeted in the NP cells of middle-aged mice. At around 11 months old, mice were gavaged with tamoxifen twice and aged for five months. HnE staining showed dramatic histological changes in the lumbar disc of SHH cKO compared to the same levels in controls at the end of the experiment (FIG. 12a). To confirm that the histological changes in the SHH cKO disc were due to loss of SHH and its targets, immunofluorescence analysis for SHH in the lumbar discs of the controls and the SHH cKO groups (FIG. 12b) was performed. SHH expression was detectable in the control disc, but not in the SHH cKO discs. Also, immunofluorescence analysis showed loss of ECM marker ACAN in the lumbar discs of the controls and SHH cKOs (FIG. 12c). These studies validate the hypothesis that the degeneration and aging of the intervertebral disc are due to loss of SHH and that SHH is crucial for maintenance of disc health.

Conditional and Transient Overexpression of SHH Expression in Adult Mice Delays Intervertebral Aging While the complete knockout of SHH accelerates aging, normally aging mice are capable of delaying degeneration when provided minimal continued SHH expression. Towards this, SHH was transiently overexpressed by generating triple mutants carrying $CK19^{CreERT2/+}$ (Means et al., 2008), $Gt(ROSA)26Sor^{tm1(rtTA)Nagy}$ (Belteki et al., 2005), and $(tetO)7CMV-rSHH^{Tg}$ (Miller et al., 2004), alleles. At 11 months of age, rtTA was activated in CK19-expressing NP cells following tamoxifen administration. And from 12-13 months of age, the mice were given doxycycline in drinking water to stimulate the expression of rSHH from the (tetO) 7CMV-rSHH allele, called rSHH-pulsed from here on. The control mice did not have the same genetic combination and did not have rSHH expression. The mice then aged 18 months. FIG. 13a shows the lumbar disc of control and rSHH-pulsed mice at 18 months of age. The control mouse disc shows signs of age-related degeneration including the reduction of NP space, very few cells in the disc, and loss of AF layers and structure. In contrast, the rSHH-pulsed disc looked very healthy with reticular and spread NP cells, and organized layers of AF cells. Immunostaining for SHH (shown by red in FIG. 13a) shows that stimulating the expression of rSHH from 12-13 months of age reprogramed the NP to continue making more SHH in these discs. Immunostaining for ECM marker ACAN (FIG. 13b) shows that conditional and transient overexpression of SHH resulted in maintenance of ECM in the disc. These results suggest that transient exposure of middle-aged mice discs to SHH can reactivate the disc and delay their aging, by maintaining disc structure, cell number, and ECM production.

Small Molecule Agonist of Hedgehog Signaling can Reactivate the Middle-Aged Mouse Disc To test the potential for activation of SHH or SHH signaling for disc therapy and treatment of lower back pain, a small molecule agonist of hedgehog signaling pathway called SAG that activates the smoothened receptor downstream of the ligand was administered to mice. Adult mice were administered intraperitoneally either with water or SAG dissolved in water at a concentration of with 10 mg/kg body weight. The mice were treated every day for seven days. Next day, the lumbar discs were collected for RNA isolation and real-time RT-qPCR analysis for SHH and its downstream targets. RT-qPCR analysis shows (FIG. 14) that injecting mice with SAG increased the mRNA expression of SHH compared to controls. Upregulation of SHH mRNA expression was also associated with an increase in the expression of its downstream targets Ptch1 and Gli1. And increase in the SHH signaling results in increased expression of ECM markers like Sox9, and Col2. These results provide evidence that although the disc is the largest avascular structure in the body, systemic delivery of hedgehog agonists can successfully activate the SHH signaling pathway in the intervertebral disc.

SHH is Expressed by Human NP Cells and its Expression Decreases with Age

To determine the potential of targeting SHH signaling and its downstream targets for regenerating human intervertebral discs, first, the mRNA expression of SHH in NP cells that were otherwise discarded as surgical waste were tested. Such samples included NP cells collected from both young and aged patients. FIG. 15 shows that human NP cells from young patients express SHH, but the expression of SHH reduces with age. This analysis shows that the mice and human disc are molecularly similar with both losing SHH expression with aging. Hence, such findings indicate that reactivation of age mouse disc by targeting SHH signaling may have a similar effect in patients.

Loss of Bra is Associated with Loss of SHH in Human NP Cells and Pathological Changes in the NP of Neonatal Mice Conditional targeting of SHH ($SHH^{flx/flx}$) in the NP cells of 11-month old mice using tamoxifen inducible $CK19^{CreERT2/+}$ line showed a phenotype similar to an aged disc within five months of SHH loss (FIG. 16A). Immunostaining show loss of Bra expression following SHH targeting (FIG. 16B).

Mouse lines with $Bra^{FloxD/WT}$ (Bra-HET) allele and Bra conditional alleles of Bra ($Bra^{flx/flx}$) were generated. Histological analysis was performed on the mid-coronal sections of the lumbar discs from both the lines at three weeks (FIG. 17A) and 12 months of age (FIG. 17B). Bra-hets showed pathological changes like the appearance of CLCs by three weeks and accelerated aging by 12 months of age. The mice with the conditional alleles of Bra ($Bra^{flx/flx}$) maintained the normal histological structure of the disc at both ages analyzed.

Conditional targeting of Bra in neonatal mouse causes pathological changes, along will loss of markers of cell growth and differentiation by ECM production. $Bra^{flx/flx}$ was conditionally targeted in NP cells of P4 and P5 mice using tamoxifen-inducible NP-specific $CK19^{CreRT2/+}$ following treatment with 200 ug of tamoxifen per gram body weight. Lumbar spine was collected at P15. HnE staining showed clumping of NP cells and disorganized AF layer (FIG. 18A), a phenotype that was observed following blockade of SHH both in vivo and in vitro. Immunostaining for Ki67 (red) was carried out to analyze the effects on cell proliferation. Ki67+ were not detected in NP cells of the Bra-cKO compared to Bra-WT controls, although the growth plate (GP) continued to be Ki67+ in the Bra-cKO, which was expected (FIG. 18B). Immunostaining for ACAN (green), an ECM marker, was also reduced in the discs on Bra-cKO compared to Bra-WT controls (FIG. 18C). Next, the mRNA levels of Bra by qPCR analysis were determined using Mm01318249_m1 TaqMan probe that spans exon 2-3 of mouse Bra. Results show a significant reduction in the Bra mRNA levels of the Bra-cKO compared to Bra-WT littermate control, indicating efficient targeting of the gene (FIG. 18D).

All publications, patents, and patent applications cited herein are hereby incorporated herein by reference in their entirety.

VII. REFERENCES

Belteki, G., Haigh, J., Kabacs, N., Haigh, K., Sison, K., Costantini, F., Whitsett, J., Quaggin, S. E. and Nagy, A. (2005). Conditional and inducible transgene expression in mice through the combinatorial use of Cre-mediated recombination and tetracycline induction. Nucleic acids research 33, e51.

Choi, K. S., Cohn, M. J. and Harfe, B. D. (2008). Identification of nucleus pulposus precursor cells and notochordal remnants in the mouse: implications for disk degeneration and chordoma formation. Dev Dyn 237, 3953-3958.

Collaborators, G. B. D. D. H. (2015). Global, regional, and national disability-adjusted life years (DALYs) for 306 diseases and injuries and healthy life expectancy (HALE) for 188 countries, 1990-2013: quantifying the epidemiological transition. Lancet 386, 2145-2191.

Dahia, C. L., Mahoney, E. and Wylie, C. (2012). Shh signaling from the nucleus pulposus is required for the postnatal growth and differentiation of the mouse intervertebral disc. PLoS One 7, e35944.

Dahia, C. L., Mahoney, E. J., Durrani, A. A. and Wylie, C. (2009a). Intercellular signaling pathways active during intervertebral disc growth, differentiation, and aging. Spine (Phila Pa. 1976) 34, 456-462.

---- (2009b). Postnatal growth, differentiation, and aging of the mouse intervertebral disc. Spine (Phila Pa. 1976) 34, 447-455.

Harfe, B. D., Scherz, P. J., Nissim, S., Tian, H., McMahon, A. P. and Tabin, C. J. (2004). Evidence for an expansion-based temporal Shh gradient in specifying vertebrate digit identities. Cell 118, 517-528.

Hartvigsen, J., Hancock, M. J., Kongsted, A., Louw, Q., Ferreira, M. L., Genevay, S., Hoy, D., Karppinen, J., Pransky, G., Sieper, J., et al. (2018). What low back pain is and why we need to pay attention. Lancet.

Hoy, D., Bain, C., Williams, G., March, L., Brooks, P., Blyth, F., Woolf, A., Vos, T. and Buchbinder, R. (2012). A systematic review of the global prevalence of low back pain. Arthritis and rheumatism 64, 2028-2037.

Kauppila, L. I. (1995). Ingrowth of blood vessels in disc degeneration. Angiographic and histological studies of cadaveric spines. J Bone Joint Surg Am 77, 26-31.

Lewis, P. M., Dunn, M. P., McMahon, J. A., Logan, M., Martin, J. F., St-Jacques, B. and McMahon, A. P. (2001). Cholesterol modification of sonic hedgehog is required for long-range signaling activity and effective modulation of signaling by Ptc1. Cell 105, 599-612.

McCann, M. R., Tamplin, O. J., Rossant, J. and Seguin, C. A. (2012). Tracing notochord-derived cells using a Noto-cre mouse: implications for intervertebral disc development. Disease models & mechanisms 5, 73-82.

Means, A. L., Xu, Y., Zhao, A., Ray, K. C. and Gu, G. (2008). A CK19(CreERT) knockin mouse line allows for conditional DNA recombination in epithelial cells in multiple endodermal organs. Genesis 46, 318-323.

Miller, L. A., Wert, S. E., Clark, J. C., Xu, Y., Perl, A. K. and Whitsett, J. A. (2004). Role of Sonic hedgehog in patterning of tracheal-bronchial cartilage and the peripheral lung. Dev Dyn 231, 57-71.

Muzumdar, M. D., Tasic, B., Miyamichi, K., Li, L. and Luo, L. (2007). A global double-fluorescent Cre reporter mouse. Genesis 45, 593-605.

Urban, J. P. and Roberts, S. (2003). Degeneration of the intervertebral disc. Arthritis Res Ther 5, 120-130.

Vergroesen, P. P., Kingma, I., Emanuel, K. S., Hoogendoorn, R. J., Welting, T. J., van Royen, B. J., van Dieen, J. H. and Smit, T. H. (2015). Mechanics and biology in intervertebral disc degeneration: a vicious circle. Osteoarthritis and cartilage 23, 1057-1070.

Winkler, T., Mahoney, E. J., Sinner, D., Wylie, C. C. and Dahia, C. L. (2014). Wnt signaling activates Shh signaling in early postnatal intervertebral discs, and re-activates Shh signaling in old discs in the mouse. PLoS One 9, e98444.

What is claimed is:

1. A method of treating intervertebral disc degeneration at one or more intervertebral discs in a human, the method comprising administering to a human an amount of a sonic hedgehog (SHH) signaling pathway activator effective for treating intervertebral disc degeneration, wherein the SHH signaling pathway activator is selected from the following:
   (i) SAG,
   (ii) SHH
   (iii) GSA-10
   (iv) purmorpamine
   (v) a compound of the following Formula I:

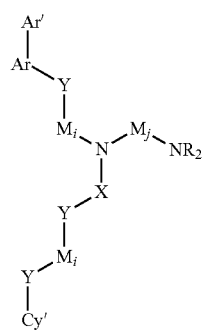

where Ar and Ar' independently represent substituted or unsubstituted aryl or heteroaryl rings; Y, independently for each occurrence, is absent or represent s-N(R)—, —O—, —S—, or —Se—; X is selected from —C(=O)—, —C(=S)—, —S(O2)-, —S(O)—, —P(=O)(OR)—, and a methylene group optionally substituted with 1-2 groups selected from lower alkyl, alkenyl, and alkynyl groups; M represents, independently for each occurrence, a substituted or un-substituted methylene group selected from —CH2-, —CHF—, —CHOH—, —CH(Me)-, and —C(=O)—, or two M taken together represent substituted or unsubstituted ethene or ethyne, wherein some or all occurrences of M in Mj form all or part of a cyclic structure; R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring optionally with N; Cy' represents a substituted or unsubstituted aryl, heterocyclyl, heteroaryl, or cycloalkyl; j represents, independently for each occurrence, an integer from 0 to 10; and i represents, independently for each occurrence, an integer from 0 to 5;

(vi) a compound of the following Formula II:

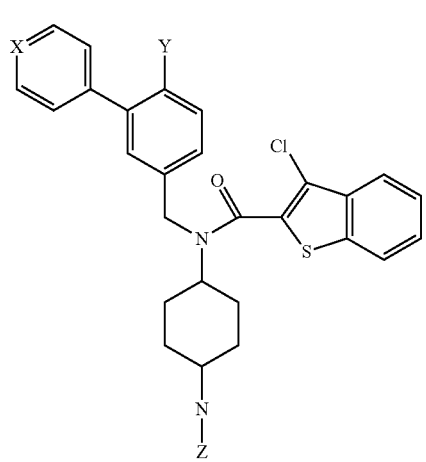

where X=C, N, or N≡C—$(CH_2)_a$—C, where 0</=a</=5; Y=R or —O—$(CH_2)_b$—$CH_3$, where 0</=b</=5; Z=H, $CH_3$ or $CH(CH_2)_c$, where 0</=c</=5, and (vii) a compound of the following Formula III:

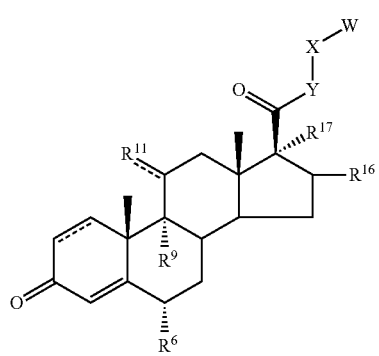

$R^6$ is selected from H and halo;
$R^9$ is selected from H and halo;
$R^{11}$ is selected from H, hydroxy, oxo and halo;
$R^{16}$ is selected from alkyl, —OR', —SR', —N(R')$_2$, —NH—C(O)R", and —NR—S(O)$_n$—R", or may be taken together with $R^{17}$ to form a ring;
$R^{17}$ is selected from hydroxy and —OC(Z)R", or may be taken together with R16 to form a ring;
Y is selected from a bond, O and S;
X is selected from a bond and CH2;
W is selected from alkyl, hydroxy, halo and —OC(O)R";
each R' is independently H, alkyl, aryl, heterocyclyl or heteroaryl;
each R" is independently alkyl;
Z is O or S; and
n is 1 or 2;
wherein when R16 and R17 are taken together to form a ring, they together form the group —O—C(Ra)2-O—, wherein each Ra is independently alkyl or two Ra are taken together to form a ring.

2. The method of claim 1, wherein the SHH signaling pathway activator is independent of a canonical Wnt signaling pathway.

3. The method of claim 2, further comprising administering an effective amount of a canonical Wnt signaling pathway activator.

4. The method claim 3, wherein the canonical Wnt signaling activator is a GSK3 inhibitor.

5. The method of claim 1, wherein administering comprises injecting into the one or more intervertebral discs, injecting into the epidural space, injecting intraperitoneally, or injecting into a nucleus pulposus of the one or more intervertebral disc.

6. The method of claim 1, wherein administering comprises systemic administration.

7. The method of claim 1 wherein the degeneration is pathological or age-related.

8. The method of claim 1, wherein the degeneration is lumbago, cervical disc disease, or thoracic disc disease.

9. The method of claim 1, wherein treating intervertebral disc degeneration comprises reversing the spinal disc degeneration or slowing the progression of spinal disc degeneration.

10. The method of claim 1, wherein treating intervertebral disc degeneration comprises reducing the pain associated with the disc degeneration or increasing the range of motion for a vertebral joint diagnosed with intervertebral disc degeneration.

11. The method of claim 1, wherein treating intervertebral disc degeneration comprises improving a measurement based on a radiographic imaging technique selected from magnetic resonance imaging, X-ray, or CT scan of a disc or vertebral used to measure degeneration as compared with a measurement prior to treatment.

12. A method for repairing or improving the function of an injured intervertebral disc or a intervertebral disc damaged from inflammation in a human subject, the method comprising administering an amount of a sonic hedgehog signaling pathway activator effective for repairing or improving the function of an intervertebral disc in the subject, wherein the SHH signaling pathway activator is selected from the following:
(i) SAG,
(ii) SHH
(iii) GSA-10
(iv) purmorpamine
(v) a compound of the following Formula I:

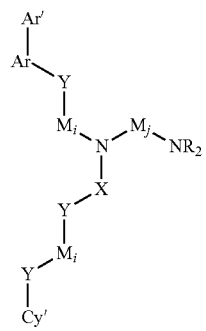

(I)

where Ar and Ar' independently represent substituted or unsubstituted aryl or heteroaryl rings; Y, independently for each occurrence, is absent or represent s-N(R)—, —O—, —S—, or —Se—; X is selected from —C(=O)—, —C(=S)—, —S(O2)-, —S(O)—, —P(=O)(OR)—, and a methylene group optionally substituted with 1-2 groups selected from lower alkyl, alkenyl, and alkynyl groups; M represents, independently for each occurrence, a substituted or un-substituted methylene group selected from —CH2-, —CHF—, —CHOH—, —CH(Me)-, and —C(=O)—, or two M taken together represent substituted or unsubstituted ethene or ethyne, wherein some or all occurrences of M in Mj form all or part of a cyclic structure; R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring optionally with N; Cy' represents a substituted or unsubstituted aryl, heterocyclyl, heteroaryl, or cycloalkyl; j represents, independently for each occurrence, an integer from 0 to 10; and i represents, independently for each occurrence, an integer from 0 to 5;

(vi) a compound of the following Formula II:

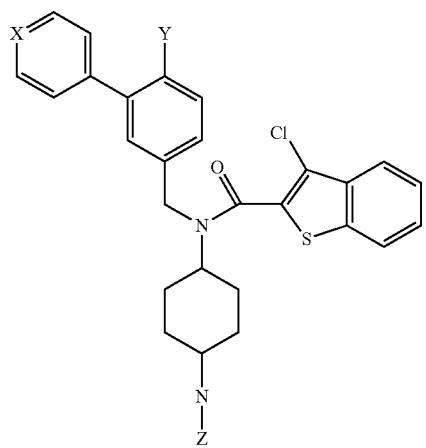

II where X=C, N, or N≡C—(CH$_2$)$_a$—C, where 0</=a</=5; Y=R or —O—(CH$_2$)$_b$—CH$_3$, where 0</=b</=5; Z=H, CH$_3$ or CH(CH$_2$)$_c$, where 0</=c</=5, and (vii) a compound of the following Formula III:

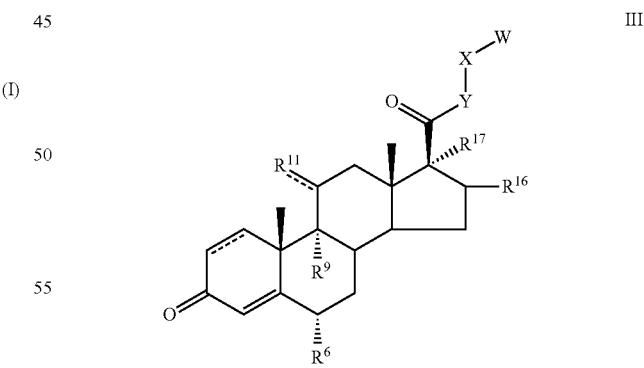

III $R^6$ is selected from H and halo;
$R^9$ is selected from H and halo;
$R^{11}$ is selected from H, hydroxy, oxo and halo;
$R^{16}$ is selected from alkyl, —OR', —SR', —N(R')$_2$, —NH—C(O)R'' and —NR—S(O)n-R'', or may be taken together with $R^{17}$ to form a ring;
$R^{17}$ is selected from hydroxy and —OC(Z)R'', or may be taken together with R16 to form a ring;

Y is selected from a bond, O and S;
X is selected from a bond and CH2;
W is selected from alkyl, hydroxy, halo and —OC(O)R";
each R' is independently H, alkyl, aryl, heterocyclyl or heteroaryl;
each R" is independently alkyl;
Z is O or S; and
n is 1 or 2;
wherein when R16 and R17 are taken together to form a ring, they together form the group —O—C(Ra)2-O—, wherein each Ra is independently alkyl or two Ra are taken together to form a ring.

13. A method for alleviating one or more symptoms of an intervertebral disc degeneration in a human subject, the method comprising administering an amount of a sonic hedgehog signaling pathway activator effective for alleviating one or more symptoms of an intervertebral disc degeneration in the subject, wherein the SHH signaling pathway activator selected from the following:

(viii) SAG,
(ix) SHH
(x) GSA-10
(xi) purmorpamine
(xii) a compound of the following Formula I:

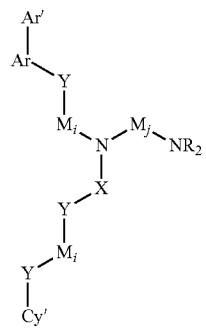

(I)

where Ar and Ar' independently represent substituted or unsubstituted aryl or heteroaryl rings; Y, independently for each occurrence, is absent or represent s-N(R)—, —O—, —S—, or —Se—; X is selected from —C(=O)—, —C(=S)—, —S(O2)-, —S(O)—, —P(=O)(OR)—, and a methylene group optionally substituted with 1-2 groups selected from lower alkyl, alkenyl, and alkynyl groups; M represents, independently for each occurrence, a substituted or un-substituted methylene group selected from —CH2-, —CHF—, —CHOH—, —CH(Me)-, and —C(=O)—, or two M taken together represent substituted or unsubstituted ethene or ethyne, wherein some or all occurrences of M in Mj form all or part of a cyclic structure; R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring optionally with N; Cy' represents a substituted or unsubstituted aryl, heterocyclyl, heteroaryl, or cycloalkyl; j represents, independently for each occurrence, an integer from 0 to 10; and i represents, independently for each occurrence, an integer from 0 to 5;

(xiii) a compound of the following Formula II:

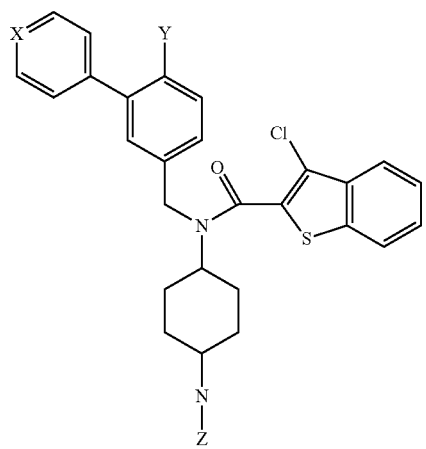

II where X=C, N, or N≡C—$(CH_2)_a$—C, where $0 </= a </= 5$; Y=R or —O—$(CH_2)_b$—$CH_3$, where $0 </= b </= 5$; Z=H, $CH_3$ or $CH(CH_2)_c$, where $0 </= c </= 5$, and (xiv) a compound of the following Formula III:

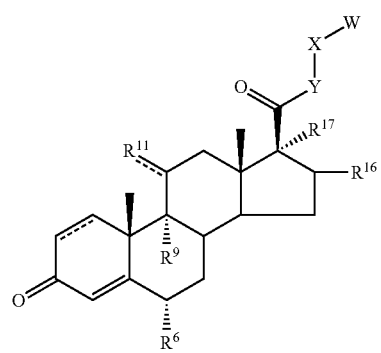

III $R^6$ is selected from H and halo;
$R^9$ is selected from H and halo;
$R^{11}$ is selected from H, hydroxy, oxo and halo;
$R^{16}$ is selected from alkyl, —OR', —SR', —N(R')$_2$, —NH—C(O)R" and —NR—S(O)n-R", or may be taken together with $R^{17}$ to form a ring;
$R^{17}$ is selected from hydroxy and —OC(Z)R", or may be taken together with R16 to form a ring;
Y is selected from a bond, O and S;
X is selected from a bond and CH2;
W is selected from alkyl, hydroxy, halo and —OC(O)R";
each R' is independently H, alkyl, aryl, heterocyclyl or heteroaryl;
each R" is independently alkyl;
Z is O or S; and
n is 1 or 2;
wherein when R16 and R17 are taken together to form a ring, they together form the group —O—C(Ra)2-O—, wherein each Ra is independently alkyl or two Ra are taken together to form a ring.

14. The method of claim 1, further comprising administering an effective amount of a canonical Wnt signaling pathway activator.

* * * * *